United States Patent [19]
Patsch et al.

[11] Patent Number: 5,929,217
[45] Date of Patent: *Jul. 27, 1999

[54] REACTIVE DYES WITH A BENZO-FUSED HETEROCYCLE AS ANCHOR

[75] Inventors: Manfred Patsch, Wachenheim; Hermann Löffler; Claus Marschner, both of Speyer, all of Germany

[73] Assignee: BASF Aktiengesellschaft, Ludwigshafen, Germany

[*] Notice: This patent is subject to a terminal disclaimer.

[21] Appl. No.: 08/620,306

[22] Filed: Mar. 22, 1996

[30] Foreign Application Priority Data

Mar. 24, 1995 [DE] Germany .................... 195 10 888

[51] Int. Cl.$^6$ .................... C09B 62/006; C09B 62/08; C09B 62/507; C09B 62/44; C09B 62/22

[52] U.S. Cl. .................... 534/618; 534/619; 534/629; 534/632; 534/634; 534/635; 534/636; 534/637; 534/638; 534/640; 534/641; 534/642; 540/123; 544/99; 548/546; 548/472; 548/475; 548/478; 548/479

[58] Field of Search .................... 534/634, 635, 534/636, 637, 638, 641, 647, 618, 619, 629; 548/546; 540/123; 544/99

[56] References Cited

U.S. PATENT DOCUMENTS

| | | | |
|---|---|---|---|
| Re. 29,640 | 5/1978 | Lamm et al. | 260/294.9 |
| 3,562,292 | 2/1971 | Grewe et al. | 260/326 |
| 3,856,772 | 12/1974 | Dunkelmann et al. | 260/154 |
| 3,907,769 | 9/1975 | Dehnert et al. | 260/156 |
| 4,532,323 | 7/1985 | Jäger | 544/75 |
| 4,923,988 | 5/1990 | Nahr et al. | 544/74 |
| 5,004,807 | 4/1991 | Pandl et al. | 260/294.9 |
| 5,491,232 | 2/1996 | Patsch et al. | 544/3 |
| 5,532,345 | 7/1996 | Herzig et al. | 534/612 |
| 5,576,445 | 11/1996 | Herzig et a. | 548/477 |

FOREIGN PATENT DOCUMENTS

| | | |
|---|---|---|
| 0 141 359 | 5/1985 | European Pat. Off. . |
| 0 311 969 | 4/1989 | European Pat. Off. . |
| 0 315 046 | 5/1989 | European Pat. Off. . |
| 0 680 951 | 11/1995 | European Pat. Off. . |
| A-680 951A2 | 11/1995 | European Pat. Off. . |
| A-680 951A3 | 11/1995 | European Pat. Off. . |
| A-685 464A1 | 12/1995 | European Pat. Off. . |
| A-688 832A2 | 12/1995 | European Pat. Off. . |
| A-688 832A3 | 12/1995 | European Pat. Off. . |
| 2 202 820 | 7/1973 | Germany . |
| 2 260 827 | 7/1974 | Germany . |
| 2 308 663 | 8/1974 | Germany . |
| 3 119 349 | 12/1982 | Germany . |
| A-1113 370 | 5/1968 | United Kingdom . |

OTHER PUBLICATIONS

Frank H. Moser, et al. *The Phthalocyanines, vol. II: Manufacture and Applications*, CRC Press, Inc., Boca Raton, Florida, 1983.

K. Venkataraman. *The Chemistry of Synthetic Dyes*, vol. II, Academic Press Inc., Publishers, New York, 1952.

K. Venkataraman. *The Chemistry of Synthetic Dyes*, vol. III, Academic Press, New York and London, 1970.

*Primary Examiner*—Floyd D. Higel
*Attorney, Agent, or Firm*—Oblon, Spivak, McClelland, Maier & Neustadt, P.C.

[57] ABSTRACT

Reactive dyes of the formula I

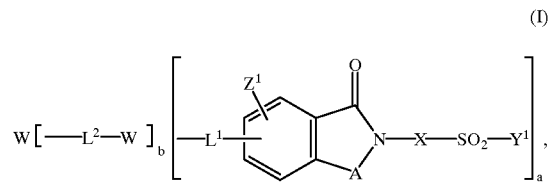

where
a is 1 or 2,
b is 0 or 1,
$Z^1$ is hydrogen, $C_1$–$C_6$-alkyl, $C_1$–$C_6$-alkoxy, halogen, nitro, amino, hydroxysulfonyl, $C_1$–$C_6$-alkoxycarbonyl, carbamoyl or $C_1$–$C_6$-mono- or dialkylcarbamoyl,
A is methylene, carbonyl, sulfonyl or a radical of the formula $CH_2$—CO or $CH_2$—$SO_2$,
X is a direct linkage or a linker,
$Y^1$ is vinyl or a radical of the formula $C_2H_4Q$ where Q is a group which can be eliminated under alkaline conditions,
W is in case 1) the radical of a chromophore which may have further reactive groups, or in case 2) the radical of a coupling component to which additionally the radical of a diazo component may be linked via an azo bridge and which may have additional reactive groups, and
$L^1$ and $L^2$ are each linkers,
their intermediates and a process for dyeing or printing substrates having hydroxyl groups or nitrogen atoms using the novel dyes are described.

6 Claims, No Drawings

REACTIVE DYES WITH A BENZO-FUSED HETEROCYCLE AS ANCHOR

The present invention relates to novel reactive dyes of the formula I

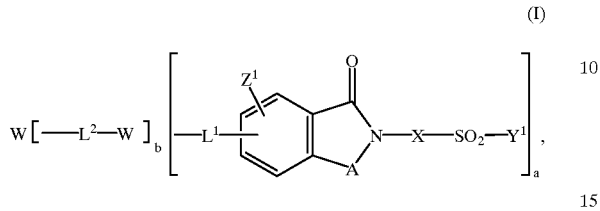

(I)

where a is 1 or 2, b is 0 or 1, $Z^1$ is hydrogen, $C_1$–$C_6$-alkyl, $C_1$–$C_6$-alkoxy, halogen, nitro, amino, hydroxysulfonyl, $C_1$–$C_6$-alkoxycarbonyl, carbamoyl or $C_1$–$C_6$-mono- or dialkylcarbamoyl, A is methylene, carbonyl, sulfonyl or a radical of the formula $CH_2$—CO or $CH_2$—$SO_2$, with the methylene group being linked in each case to the benzene ring, X is a direct linkage, $C_1$–$C_8$-alkylene which may be interrupted via 1 to 3 oxygen atoms in ether functionality, 1 to 3 imino groups or 1 to 3 $C_1$–$C_4$-alkylimino groups, or a radical of the formula $L^3$—CO—$NZ^2$—$L^4$, where $L^3$ and $L^4$ are each, independently of one another, $C_1$–$C_4$-alkylene and $Z^2$ is hydrogen, $C_1$–$C_6$-alkyl or phenyl, and $Y^1$ is vinyl or a radical of the formula $C_2H_4Q$ where Q is a group which can be eliminated under alkaline conditions, W is in case 1) the radical of a chromophore which may have further reactive groups and which is derived from a possibly metallized mono- or disazo dye, a triphendioxazine, an anthraquinone, a metallized formazan or a metallized phthalocyanine, or in case 2) the radical of a coupling component to which additionally the radical of a diazo component may be linked via an azo bridge and which may have additional reactive groups, $L^1$ is in case 1) a linker of the formula $O_2S$—$NZ^3$, OC—$NZ^3$, $Z^3N$—$O_2S$, $Z^3N$—OC, $Z^3N$—OC—$NZ^4$, $NZ^3$

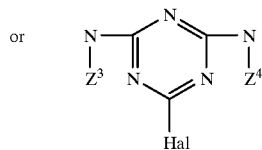

or where $Z^3$ and $Z^4$ are each, independently of one another, hydrogen, $C_1$–$C_6$-alkyl or phenyl and Hal is fluorine, chlorine or bromine or $NZ^3$ or $NZ^4$ is also piperazine-1,4-diyl, or in case 2) an azo bridge and $L^2$ is a radical of the formula

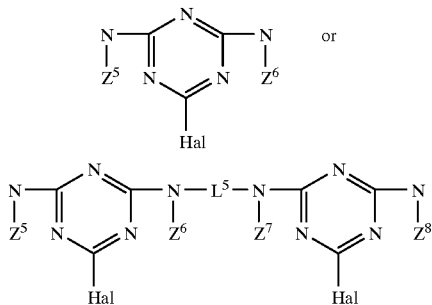

or where $Z^5$, $Z^6$, $Z^7$ and $Z^8$ are each, independently of one another, hydrogen, $C_1$–$C_6$-alkyl or phenyl and $L^5$ is $C_2$–$C_8$-alkylene or phenylene which is unsubstituted or substituted by $C_1$–$C_4$-alkyl, $C_1$–$C_4$-alkoxy or hydroxysulfonyl, and Hal has in each case the above-mentioned meaning, to the intermediates thereof and to a process for dyeing or printing substrates having hydroxyl groups or nitrogen atoms using the novel dyes.

It is an object of the present invention to provide novel reactive dyes with advantageous use properties. The novel dyes were intended to be particularly suitable for the exhaust and cold pad-batch processes and to be especially distinguished by high yield, good wet fastness properties and brilliant dyeings. In addition, the portions not fixed to the fibers were to be easy to wash off.

We have found that this object is achieved by the reactive dyes of the formula I defined at the outset.

All the alkyl and alkylene groups occurring in the above-mentioned formula may be either straight-chain or branched.

Examples of $Z^1$, $Z^2$, $Z^3$, $Z^4$, $Z^5$, $Z^6$, $Z^7$ and $Z^8$ radicals are methyl, ethyl, propyl, isopropyl, butyl, isobutyl, sec-butyl, tert-butyl, pentyl, isopentyl, neopentyl, tert-pentyl, hexyl or 2-methylpentyl.

Further examples of $Z^1$ radicals are methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, 2-methylpentyloxy, fluorine, chlorine, bromine, methoxycarbonyl, ethoxycarbonyl, propoxycarbonyl, isopropoxycarbonyl, butoxycarbonyl, isobutoxycarbonyl, sec-butoxycarbonyl, pentyloxycarbonyl, isopentyloxycarbonyl, neopentyloxycarbonyl, tert-pentyloxycarbonyl, hexyloxycarbonyl, mono- or dimethylcarbamoyl, mono- or diethylcarbamoyl, mono- or dipropylcarbamoyl, mono- or diisopropylcarbamoyl, mono- or dibutylcarbamoyl, mono- or dipentylcarbamoyl, mono- or dihexylcarbamoyl or N-methyl-N-ethylcarbamoyl.

Examples of X, $L^3$, $L^4$ and $L^5$ are $(CH_2)_2$, $(CH_2)_3$, $(CH_2)_4$, $CH(CH_3)CH_2$ or $CH(CH_3)CH(CH_3)$.

Further examples of X and $L^5$ are $(CH_2)_5$, $(CH_2)_6$, $(CH_2)_7$ or $(CH_2)_8$.

A further example of X, $L^3$ and $L^4$ is methylene.

Further examples of $L^5$ are 1,2-, 1,3- or 1,4-phenylene which can in each case be substituted once or twice by methyl, methoxy or hydroxysulfonyl.

Further examples of X radicals are $C_2H_4$—O—$C_2H_4$, $C_2H_4$—NH—$C_2H_4$, $C_2H_4$—N($CH_3$)—$C_2H_4$, $C_2H_4$—O—$C_2H_4$—O—$C_2H_4$, $C_2H_4$—NH—$C_2H_4$—NH—$C_2H_4$, $C_2H_4$—N($CH_3$)—$C_2H_4$—N($CH_3$)—$C_2H_4$, $C_2H_4$—O—$C_2H_4$—N($CH_3$)—$C_2H_4$, $C_2H_4$—O—$C_2H_4$—O—$C_2H_4$—O—$C_2H_4$, $C_2H_4$—NH—$C_2H_4$—NH—$C_2H_4$—NH—$C_2H_4$, $C_2H_4$—N($CH_3$)—$C_2H_4$—N($CH_3$)—$C_2H_4$—N($CH_3$)—

$C_2H_4$, $C_2H_4$—CO—NH—$C_2H_4$, $C_2H_4$—CO—N($CH_3$)—$C_2H_4$, $C_3H_6$—CO—NH—$C_2H_4$, $C_2H_4$—CO—NH—$C_3H_6$, $C_3H_6$—CO—NH—$C_3H_6$ or $C_3H_6$—CO—N($CH_3$)—$C_3H_6$.

The radical Q is a group which can be eliminated under alkaline conditions. Examples of such groups are chlorine, bromine, $C_1$–$C_4$-alkylsulfonyl, phenylsulfonyl, $OSO_3H$, $SSO_3H$, $OP(O)(OH)_2$, $C_1$–$C_4$-alkylsulfonyloxy, phenylsulfonyloxy, $C_1$–$C_4$-alkanoyloxy, $C_1$–$C_4$-dialkylamino or a radical of the formula

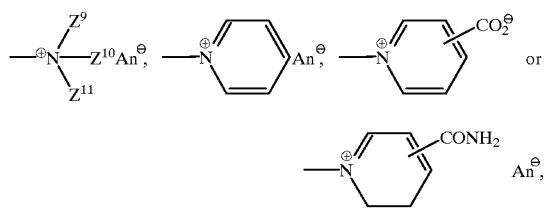

where $Z^9$, $Z^{10}$ and $Z^{11}$ are identical or different and are each, independently of one another, $C_1$–$C_4$-alkyl or benzyl and $An^{\ominus}$ is in each case one equivalent of an anion. Examples of anions which may be suitable in this case are fluoride, chloride, bromide, iodide, mono-, di- or trichloroacetate, methylsulfonate, phenylsulfonate or 2- or 4-methylphenylsulfonate.

When a is 2, the radicals

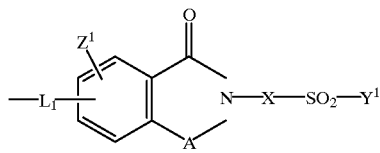

can be identical or different.

When b is 1, the W radicals can likewise be identical or different.

The fiber-reactive anchor radical of the formula II

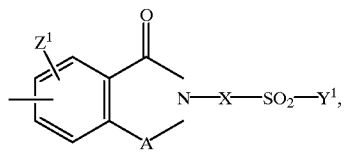

(II)

where A, X, $Y^1$ and $Z^1$ each have the abovementioned meanings is referred to as "E" hereinafter.

Preferred reactive dyes of the formula I are those where A is methylene, carbonyl or the radical of the formula $CH_2$—CO, in particular methylene.

Further preferred reactive dyes of the formula I are those where X is $C_1$–$C_8$-alkylene which may be interrupted by 1 to 3 oxygen atoms in ether functionality, and those reactive dyes of the formula I where X is $C_2$–$C_4$-alkylene or a radical of the formula $X^1$—O—$X^2$ where $X^1$ and $X^2$ are each, independently of one another, $C_2$- or $C_3$-alkylene are of particular importance.

Further preferred reactive dyes of the formula I are those where $Z^1$ is hydrogen.

Besides the anchor system E it is possible for the radical W to carry further fiber-reactive radicals. Examples of such radicals are heterocyclic anchor radicals or anchor radicals from the aliphatic series.

Examples of heterocyclic anchor radicals are halogen-containing radicals derives from the following heterocyclic parent structures: 1,3,5-triazine, quinoxaline, phthalazine, pyrimidine or pyridazine, or 2-alkylsulfonylbenzothiazole.

The following heterocyclic radicals may be mentioned particularly:

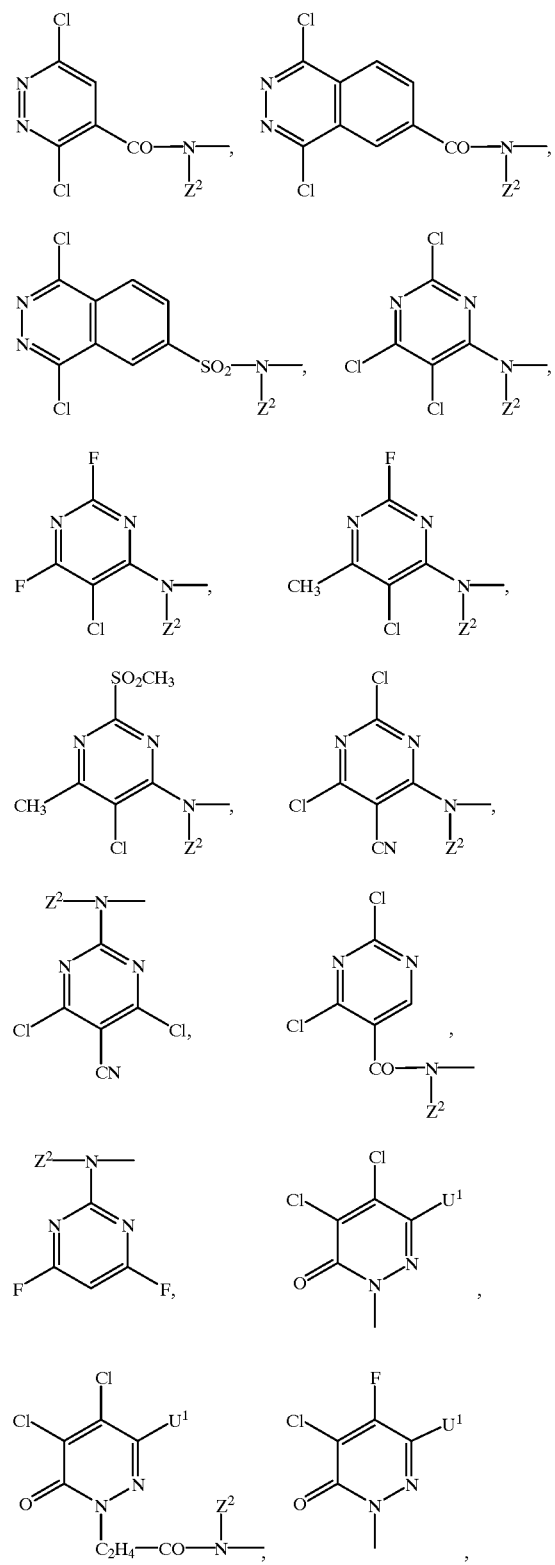

-continued

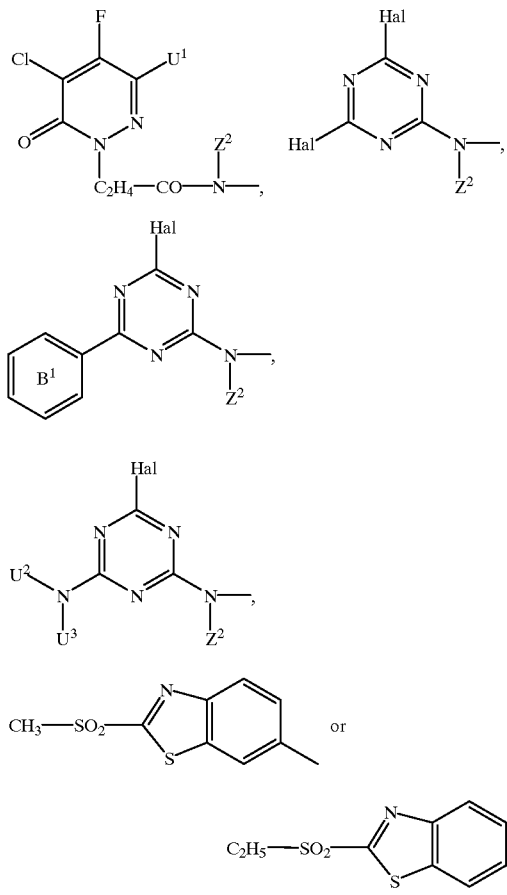

where $Z^2$ and Hal each have the abovementioned meanings, and $U^1$ is hydrogen or nitro and $U^2$ and $U^3$ are each, independently of one another, hydrogen, $C_1$–$C_6$-alkyl which is unsubstituted or substituted by hydroxyl, halogen, cyano, hydroxysulfonyl or a radical of the formula —$SO_2$—$Y^1$ where $Y^1$ has the abovementioned meaning, and can in each case be interrupted by 1 or 2 oxygen atoms in ether functionality, imino or $C_1$–$C_4$-alkylimino groups, or $U^2$ and $U^3$ together with the nitrogen atom collecting them are pyrrolidinyl, piperidinyl, morpholinyl, piperazinyl or N—($C_1$–$C_4$-alkyl)piperazinyl or $U^2$ is also a radical of the formula

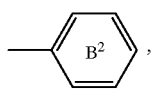

where the rings $B^1$ and $B^2$ can in each case be substituted once or twice by hydroxysulfonyl and benzo-fused, and the ring $B^2$ can, independently thereof, be substituted once or twice by chlorine, nitro, $C_1$–$C_4$-alkyl, $C_1$–$C_4$-alkoxy, cyano, carboxyl, acetylamino, hydroxysulfonylmethyl or a radical of the formula $CH_2$—$SO_2$—$Y^1$, $SO_2$—$Y^1$, NH—CO—$Y^1$ or $NU^2$—CO—$NU^2$—$L^0$—$SO_2$—$Y^1$ where $Y^1$ and $U^2$ each have the abovementioned meanings, and $L^0$ is $C_2$–$C_6$-alkylene which is unsubstituted or substituted by hydroxyl, chlorine, cyano, carboxyl, $C_1$–$C_4$-alkoxycarbonyl, $C_1$–$C_4$-alkanoyloxy or sulfato, and can be interrupted by in each case 1 or 2 oxygen atoms in ether functionality or imino or $C_1$–$C_4$-alkylimino groups.

Examples of anchor radicals from the aliphatic series are acryloyl, mono-, di- or trichloroacryloyl, mono-, di- or tri-bromoacryloyl, —CO—CCl═CH—COOH, —CO—CH═CCl—COOH, 2-chloropropionyl, 1,2-dichloropropionyl, 1,2-dibromopropionyl, 3-phenylsulfonylpropionyl, 3-methylsulfonylpropionyl, 2-sulfatoethylaminosulfonyl, 2-chloro-2,3,3-trifluorocyclobutylcarbonyl, 2,2,3,3-tetrafluorocyclobutylcarbonyl, 2,2,3,3-tetrafluorocyclobutylsulfonyl, 2-(2,2,3,3-tetrafluorocyclobutyl)acryloyl, 1- or 2-alkyl- or 1- or 2-arylsulfonylacryloyl such as 1- or 2-methylsulfonylacryloyl, or a radical of the formula $SO_2$—$Y^1$, CONH—$L^6$—$SO_2$—$Y^1$ or NHCONH—$L^6$—$SO_2$—$Y^1$ where $Y^1$ has the abovementioned meaning and $L^6$ is $C_1$–$C_4$-alkylene or phenylene.

W in formula I is, for example, the radical of a coupling component to which additionally the radical of a diazo component may be linked via an azo bridge and which may have additional reactive groups. In this case, the anchor radical E is linked to the radical W via an azo bridge (—N═N—).

Dyes of this class obey, for example, the formula IIIa or IIIb $$(E—N═N—)_a K \qquad (IIIa)$$

$$E—N═N—K—N═N—D, \qquad (IIIb)$$

where K is the radical of a coupling component, D is the radical of a diazo component and a is 1 or 2, and E has the abovementioned meaning. When the radical E occurs twice in the formula IIIa (a=2), the E radicals can be either identical or different.

Examples of valuable dyes of this class are water-soluble azo dyes, in particular monoazo dyes of the formula IIIa (a=1) or disazo dyes of the formula IIIa (a=2) or IIIb, which have hydroxysulfonyl and/or carboxyl groups.

Important coupling components HK are derived, for example, from compounds of the benzene, naphthalene, pyrazole, pyridine, pyrimidine, indole or N-arylacetoacetamide series.

Important diazo components D—$NH_2$ are derived, for example, from compounds of the aniline or aminonaphthalene series.

Particularly preferred dyes are those of the formula IV $$E—N═N—K^1, \qquad (IV)$$

where E has the abovementioned meanings and $K^1$ is the radical of a coupling component of the benzene, naphthalene, pyrazole or pyridine series which may have further fiber-reactive groups, in particular the group E, the group of the formula $SO_2$—$Y^1$ where $Y^1$ has the abovementioned meaning, or those of the halotriazine series.

Further particularly preferred dyes are those of the formula V

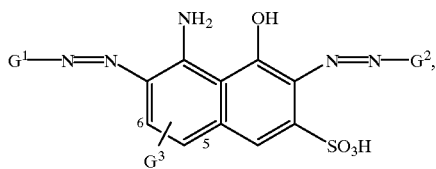

(V)

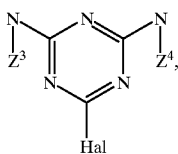

(IV)

where one of the two radicals $G^1$ and $G^2$ is the radical E, where this has the abovementioned meaning, and the other is the radical $D^1$, where this is a radical of a diazo component of the aniline or naphthalene series, which may have further fiber-reactive groups, in particular the group E, the group of the formula $SO_2$—$Y^1$ where $Y^1$ has the abovementioned meaning, or those of the halotriazine series, and $G^3$ is hydroxysulfonyl in ring position 5 or 6.

W in formula I is furthermore, for example, the radical, which may be metallized, of an azo dye. Suitable azo dyes from which such radicals are derived are known, and large numbers have been described, eg. in K. Venkataraman "The Chemistry of Synthetic Dyes", Vol. VI, Academic Press, New York, London, 1972. The azo dyes obey the formula VI

(VI)

where D is the radical of a diazo component, K is the radical of a coupling component and l is 0 or 1, with the D radicals being identical or different when l is 1.

Valuable dyes from which the radical W is derived are, for example, water-soluble azo dyes, in particular monoazo dyes of the formula VI (l=0) which may have hydroxysulfonyl and/or carboxyl groups.

The radical W is preferably derived from non-metallized azo dyes, in particular from those which contain sulfo and/or carboxyl groups, with those which have 1 to 6 sulfo groups being particularly emphasized.

Important azo dyes from which the radical W is derived are, for example, those of the phenylazonaphthalene, phenylazo-1-phenyl-5-pyrazolone, phenylazobenzene, naphthylazobenzene, phenylazoaminonaphthalene, naphthylazonaphthalene, naphthylazo-1-phenyl-5-pyrazolone, phenylazopyridone, phenylazoaminopyridine, naphthylazopyridone, naphthylazoaminopyridine or stilbylazobenzene series.

Particular preferred reactive dyes are those of the formula VII

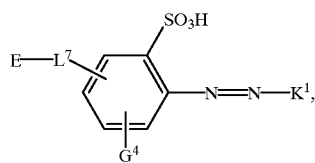

(VII)

where E and $K^1$ each have the abovementioned meanings, $L^7$ is a radical of the formula $O_2S$—$NZ^3$, OC—$NZ^3$, $Z^3N$—$O_2S$, $Z^3N$—OC, $Z^3N$—OC—$NZ^4$, $NZ^3$ or where $Z^3$, $Z^4$ and Hal each have the abovementioned meanings and $G^4$ is hydrogen, $C_1$–$C_4$-alkyl, $C_1$–$C_4$-alkoxy, chlorine or hydroxysulfonyl.

Further particularly preferred reactive dyes are those of the formula VIII

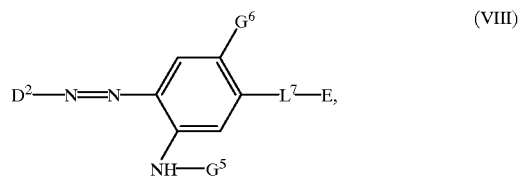

(VIII)

where E and $L^7$ each have the abovementioned meanings, $G^5$ is $C_1$–$C_4$-alkanoyl, carbamoyl, $C_1$–$C_4$-mono- or dialkylcarbamoyl, phenylcarbamoyl or cyclohexylcarbamoyl, $G^6$ is hydrogen, $C_1$–$C_4$-alkyl, $C_1$–$C_4$-alkoxy, hydroxysulfonyl or chlorine and $D^2$ is the radical of a diazo component of the aniline or naphthalene series which has no further fiber-reactive group.

Further particularly preferred reactive dyes are those of the formula IX

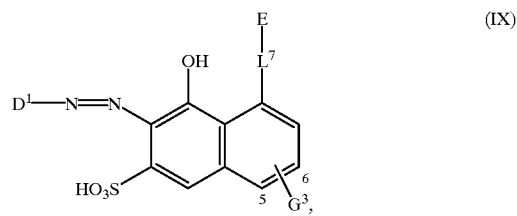

(IX)

where $D^1$, E and $L^7$ each have the abovementioned meanings, and $G^3$ is hydroxysulfonyl in ring position 5 or 6.

Further particularly preferred reactive dyes are those of the formula X

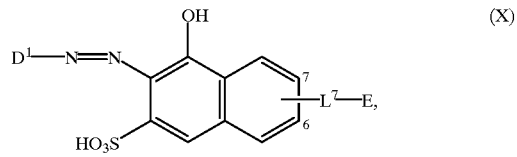

(X)

where $D^1$, E and $L^7$ each have the abovementioned meanings, and the group —$L^7$—E is in ring position 6 or 7.

Further valuable compounds are those of the formula XI (XI)

$$D^2-N=N-\underset{(SO_3H)_p}{\text{naphthyl}}-N=N-\underset{(SO_3H)_r}{\text{naphthyl}}-L^7-E,$$

where $D^2$, E and $L^7$ each have the abovementioned meanings, and p and r are each, independently of one another, 0, 1 or 2.

Further valuable compounds are those of the formula XII (XII)

$$G^7-N=N-\underset{G^3}{\underset{5}{\overset{6}{\text{naphthyl}}}}\underset{SO_3H}{\overset{NH_2\ OH}{-}}N=N-G^8,$$

where $G^3$ has the abovementioned meaning, and one of the two radicals $G^7$ and $G^8$ is the radical $D^1$, where this has the abovementioned meaning, and the other is the radical $$\underset{HO_3S}{\text{phenyl}}-L^7-E,$$

or else both radicals $G^7$ and $G^8$ are the radical $$\underset{HO_3S}{\text{phenyl}}-L^7-E,$$

where $L^7$ and E each have the abovementioned meanings.

Those aromatic radicals $D^1$ and $D^2$ of diazo components of the aniline or aminonaphthalene series which have no fiber-reactive groups are derived, for example, from amines of the formulae XIIIa–f (XIIIa)

$$\underset{R^2\ (SO_3H)_p}{\overset{R^1\ NH_2}{\text{phenyl}}},$$

(XIIIb)

$$\underset{}{\overset{R^1\ R^2\ (SO_3H)_m}{\text{naphthyl}}-NH_2},$$

(XIIIc)

$$\underset{}{\overset{OH\ (SO_3H)_m}{\text{naphthyl}}-NH_2},$$

(XIII)d $$\underset{R^1}{\overset{R^2}{\text{phenyl}}}-F^1-\underset{R^1}{\overset{R^2}{\text{phenyl}}}-NH_2,$$

(XIII)e $$NH_2-\underset{R^2}{\overset{R^1}{\text{phenyl}}}-\left[F^1-\underset{R^2}{\overset{R^1}{\text{phenyl}}}\right]_q-NH_2,$$

(XIIIf)

$$\underset{}{\overset{R^1\ R^2\ NH_2}{\text{naphthyl}}-NH_2},$$

where m is 0, 1, 2 or 3, p is 0, 1 or 2, q is 0 or 1, $R^1$ is hydrogen, $C_1$–$C_4$-alkyl, $C_1$–$C_4$-alkoxy, acetyl, cyano, carboxyl, hydroxysulfonyl, $C_1$–$C_4$-alkoxycarbonyl, hydroxyl, carbamoyl, $C_1$–$C_4$-mono- or dialkylcarbamoyl, fluorine, chlorine, bromine or trifluoromethyl, $R^2$ is hydrogen, $C_1$–$C_4$-alkyl, $C_1$–$C_4$-alkoxy, cyano, carboxyl, hydroxysulfonyl, acetylamino, $C_1$–$C_4$-alkoxycarbonyl, carbamoyl, $C_1$–$C_4$-mono- or dialkylcarbamoyl, fluorine, chlorine, nitro, sulfamoyl, $C_1$–$C_4$-mono- or dialkylsulfamoyl, $C_1$–$C_4$-alkylsulfonyl, phenylsulfonyl or phenoxy and $F^1$ is a direct linkage, oxygen, sulfur or a radical of the formula —NHCO—, —NHCONH—, —CONH—, —CO—, —NHSO$_2$—, —SO$_2$NH—, —SO$_2$—, —CH=CH—, —CH$_2$—CH$_2$—, —CH$_2$—, —NH—, or —N=N—.

Preferred components in this connection are those where $R^1$ is hydrogen, methyl, methoxy, carboxyl, hydroxysulfonyl, hydroxyl or chlorine, $R^2$ is hydrogen, methyl, methoxy, carboxyl, hydroxysulfonyl, acetylamino or chlorine and $F^1$ is a radical of the formula —CO—, —SO$_2$—, —CH=CH—, —CH$_2$—CH$_2$—, —CH$_2$— or —N=N—.

Aromatic amines which are suitable as diazo components and correspond to the formula XIIIa, XIIIb, XIIIc or XIIId are for example aniline, 2-methoxyaniline, 2-methylaniline, 4-chloro-2-aminoanisole, 4-methylaniline, 4-methoxyaniline, 2-methoxy-5-methylaniline, 2,5-dimethoxyaniline, 2,5-dimethylaniline, 2,4-dimethylaniline, 2,5-diethoxyaniline, 2-chloroaniline, 3-chloroaniline, 4-chloroaniline, 2,5-dichloroaniline, 4-chloro-2-nitroaniline, 4-chloro-2-methylaniline, 3-chloro-2-methylaniline, 4-chloro-2-aminotoluene, 4-phenylsulfonylaniline, 2-ethoxy-1-naphthylamine, 1-naphthylamine, 2-naphthylamine, 4-methylsulfonylaniline, 2,4-dichloroaniline-5-carboxylic acid, 2-aminobenzoic acid, 4-aminobenzoic acid, 3-aminobenzoic acid, 3-chloroaniline-6-carboxylic acid, aniline-2- or -3- or -4-sulfonic acid, aniline-2,5-disulfonic acid, aniline-2,4-disulfonic acid, aniline-3,5-disulfonic acid, 2-aminotoluene-4-sulfonic acid, 2-aminoanisole-4-sulfonic acid, 2-aminoanisole-5-sulfonic acid, 2-ethoxyaniline-5-sulfonic acid, 2-ethoxyaniline-4-sulfonic acid, 4-hydroxysulfonyl-2-aminobenzoic acid, 2,5-dimethoxyaniline-4-sulfonic acid, 2,4-dimethoxyaniline-5-sulfonic acid, 2-methoxy-5-methylaniline-4-sulfonic acid, 4-aminoanisole-3-sulfonic acid, 4-aminotoluene-3-sulfonic acid, 2-aminotoluene-5-sulfonic acid, 2-chloroaniline-4-sulfonic acid, 2-chloroaniline-5-sulfonic acid, 2-bromoaniline-4-sulfonic acid, 2,6-dichloroaniline-4-sulfonic acid, 2,6-dimethylaniline-3- or -4-sulfonic acid, 3-acetylaminoaniline-6-sulfonic acid, 4-acetylaminoaniline-2-sulfonic acid, 1-aminonaphthalene-4-sulfonic acid, 1-aminonaphthalene-3-sulfonic acid, 1-aminonaphthalene-5-sulfonic acid, 1-aminonaphthalene-6-sulfonic acid, 1-aminonaphthalene-7-sulfonic acid, 1-aminonaphthalene-3,7-disulfonic acid, 1-aminonaphthalene-3,6,8-trisulfonic acid, 1-aminonaphthalene-4,6,8-trisulfonic acid, 2-naphthylamine-5- or -6- or -8-sulfonic acid, 2-aminonaphthalene-3,6,8-trisulfonic acid, 2-aminonaphthalene-6,8-disulfonic acid, 2-aminonaphthalene-1,6-disulfonic acid, 2-aminonaphthalene-1-sulfonic acid, 2-aminonaphthalene-1,5-disulfonic acid, 2-aminonaphthalene-3,6-disulfonic acid, 2-aminonaphthalene-4,8-disulfonic acid, 2-aminophenol-4-sulfonic acid, 2-aminophenol-5-sulfonic acid, 3-aminophenol-6-sulfonic acid, 1-hydroxy-2-aminonaphthalene-5,8- or -4,6-disulfonic acid, 4-aminodiphenylamine, 4-amino-4'-methoxydiphenylamine, 4-amino-4'-methoxydiphenylamine-3-sulfonic acid, 4-(2-methylphenylazo)-2-methylaniline, 4-aminoazobenzene, 4-nitrophenylazo-1-aminonaphthalene, 4-(6-hydroxysulfonylnaphthylazo)-1-aminonaphthalene, 4-(2,5-dihydroxysulfonylphenylazo)-1-aminonaphthalene, 4'-amino-3'-methyl-3-nitrobenzophenone, 4-aminobenzophenone, 4-(4-aminophenylazo) benzenesulfonic acid, 4-(4-amino-3-methoxyphenylazo) benzenesulfonic acid or 2-ethoxy-1-naphthylamine-6-sulfonic acid.

Aromatic diamines which are suitable as tetraazo components or else for doubling (eg. with cyanuric chloride) and which correspond to the formula XIIIe or XIIIf are, for example, 1,3-diaminobenzene, 1,3-diaminobenzene-4-sulfonic acid, 1,4-diaminobenzene, 1,4-diaminobenzene-2-sulfonic acid, 1,4-diamino-2-methylbenzene, 1,4-diamino-2-methoxybenzene, 1,3-diamino-4-methylbenzene, 1,3-diaminobenzene-5-sulfonic acid, 1,3-diamino-5-methylbenzene, 1,6-diaminonaphthalene-4-sulfonic acid, 2,6-diaminonaphthalene-4,8-disulfonic acid, 3,3'-diaminodiphenyl sulfone, 4,4'-diaminodiphenyl sulfone, 4,4'-diaminostilbene-2,2'-disulfonic acid, 2,2'-diaminodiphenyl sulfone, 2,2'-diamino-4,5-disulfodiphenyl sulfone, 4,4'-diaminobenzophenone, 4,4'-diamino-3,3'-dinitrobenzophenone, 3,3'-diamino-4,4'-dichlorobenzophenone, 4,4'- or 3,3'-diaminodiphenyl, 4,4'-diamino-3,3'-dichlorodiphenyl, 4,4'-diamino-3,3'-dimethoxy- or -3,3'-dimethyl- or -2,2'-dimethyl- or -2,2'-dichloro- or -3,3'-diethoxydiphenyl, 4,4'-diamino-3,3'-dimethyl-6,6'-dinitrodiphenyl, 4,4'-diaminodiphenyl-2,2'- or -3,3'-disulfonic acid, 4,4'-diamino-3,3'-dimethyl- or -3,3'-dimethoxy- or -2,2'-dimethoxydiphenyl-6,6'-disulfonic acid, 4,4'-diamino-2,2',5,5'-tetrachlorodiphenyl, 4,4'-diamino-3,3'-dinitrodiphenyl, 4,4'-diamino-2,2'-dichloro-5,5'-dimethoxydiphenyl, 4,4'-diaminodiphenyl-2,2'- or -3,3'-dicarboxylic acid, 4,4'-diamino-3,3'-dimethyldiphenyl-5,5'-disulfonic acid, 4,4'-diamino-2-nitrodiphenyl, 4,4'-diamino-3-ethoxy- or -3-hydroxysulfonyldiphenyl, 4,4'-diamino-3,3'-dimethyldiphenyl-5-sulfonic acid, 4,4'-diaminodiphenylmethane, 4,4'-diamino-3,3'-dimethyldiphenylmethane, 4,4'-diamino-2,2',3,3'-tetramethyldiphenylmethane, 4,4'-diaminodiphenylethane, 4,4'-diaminostilbene or 4,4'-diaminodiphenylmethane-3,3'-dicarboxylic acid.

Those aromatic radicals $D^1$ of diazo components from the aniline or aminonaphthalene series which may carry further fiber-reactive radicals are derived, for example, from amines of the formulae XIVa–c

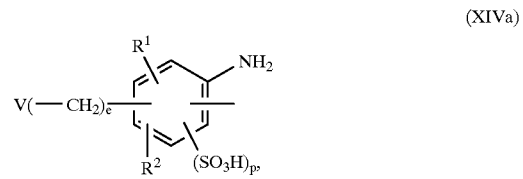

(XIVa)

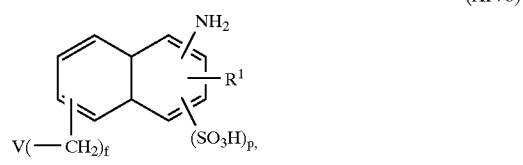

(XIVb)

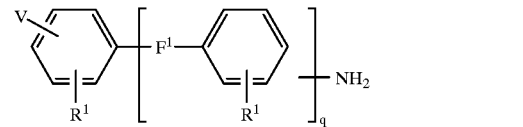

(XIVc)

where $R^1$, $R^2$, p, q and $F^1$ each have the abovementioned meanings, and e and f are identical or different and are each, independently of one another, 0 or 1, and V is a fiber-reactive radical.

Fiber-reactive radicals V are derived, for example, from the radical E or are, as stated above, heterocyclic anchor radicals or anchor radicals from the aliphatic series.

Examples of aromatic amines on which the derivatives of the formula XIVa, XIVb or XIVc having the fiber-reactive radical V are based are 1,3-diaminobenzene, 1,3-diaminobenzene-4-sulfonic acid, 1,3-diaminobenzene-4,6-disulfonic acid, 1,4-diaminobenzene, 1,4-diaminobenzene-2-sulfonic acid, 1,4-diaminobenzene-2,5-disulfonic acid, 1,4-diamino-2-methylbenzene, 1,4-diamino-2-methoxybenzene, 1,3-diamino-4-methylbenzene, 1,4-diaminobenzene-2,6-disulfonic acid, 1,5-diamino-4-methylbenzene-2-sulfonic acid, 1,5-diamino-4- methoxybenzene-2-sulfonic acid, 1,6-diamino-2-naphthol-4-sulfonic acid, 1,6-diaminonaphthalene-4-sulfonic acid, 2,6-diaminonaphthalene-4,8-disulfonic acid, 2,6-diamino-1-naphthol-4,8-disulfonic acid, 1,3-diaminobenzene-5-sulfonic acid, 1,3-diamino-5-methylbenzene, 2,6-diaminophenol-4-sulfonic acid, 5-aminomethyl-2-aminonaphthalene-1-sulfonic acid, 5-(N-methylaminomethyl)-2-aminonaphthalene-1-sulfonic acid, 4,4-diaminostilbene-3,3-dicarboxylic acid, 4-(N-methylaminomethyl)aniline-2-sulfonic acid or 3-(N-methylaminomethyl)aniline-6-sulfonic acid.

The K radicals of the coupling component are preferably derived from the benzene, naphthalene, pyrazole, pyridine, pyrimidine, indole or N-arylacetoacetamide series and may also carry fiber-reactive groups.

Coupling components of the aniline or naphthalene series without fiber-reactive groups correspond, for example, to the compounds of the formulae XVa–g

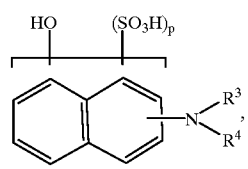
(XV a)

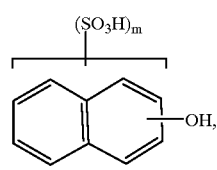
(XV b)

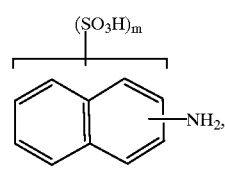
(XV c)

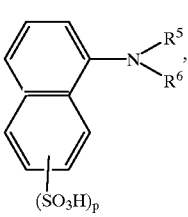
(XV d)

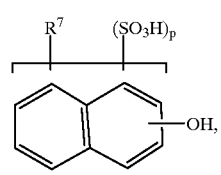
(XV e)

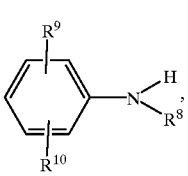
(XV f)

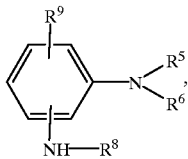
(XV g)

where $R^3$ is hydrogen or $C_1$–$C_4$-alkyl, $R^4$ is hydrogen, $C_1$–$C_4$-alkyl or phenyl which can be substituted once or twice by $C_1$–$C_4$-alkyl, $C_1$–$C_4$-alkoxy, chlorine, bromine or hydroxysulfonyl, $R^5$ is hydrogen or $C_1$–$C_4$-alkyl which can be substituted by hydroxyl, cyano, carboxyl, hydroxysulfonyl, sulfato, methoxycarbonyl, ethoxycarbonyl or acetoxy, $R^6$ is hydrogen, $C_1$–$C_4$-alkyl which can be substituted by hydroxyl, cyano, carboxyl, hydroxysulfonyl, sulfato, methoxycarbonyl, ethoxycarbonyl or acetoxy, or benzyl or phenyl which can be substituted by $C_1$–$C_4$-alkyl, $C_1$–$C_4$-alkoxy, chlorine or hydroxysulfonyl, $R^7$ is $C_1$–$C_6$-alkylureido, phenylureido which can be substituted by chlorine, methyl, methoxy, nitro, hydroxysulfonyl or carboxyl, or $C_1$–$C_6$-alkanoylamino which can be substituted by hydroxysulfonyl or chlorine, or cyclohexanecarbonylamino, benzoylamino which can be substituted by chlorine, methyl, methoxy, nitro, hydroxysulfonyl or carboxyl, or hydroxyl, $R^8$ is hydrogen, $C_1$–$C_6$-alkyl, in particular $C_1$–$C_4$-alkyl, which can in each case be substituted by phenyl, $C_1$–$C_4$-alkoxy, hydroxyl, phenoxy or $C_1$–$C_4$-alkanoyloxy, or $C_5$–$C_7$-cycloalkyl, hydroxysulfonylphenyl, $C_1$–$C_4$-alkanoyl, carbamoyl, $C_1$–$C_4$-mono- or di-alkylcarbamoyl, phenylcarbamoyl or cyclohexylcarbamoyl, $R^9$ is $C_1$–$C_4$-alkoxy, chlorine, bromine, hydroxysulfonyl, $C_1$–$C_4$-alkanoylamino, amino, ureido, methylsulfonylamino, ethylsulfonylamino, dimethylaminosulfonylamino, methylamino, ethylamino, dimethylamino or diethylamino and $R^{10}$ is hydrogen, $C_1$–$C_4$-alkyl, $C_1$–$C_4$-alkoxy, hydroxysulfonyl, chlorine or bromine, and p and m each have the abovementioned meanings.

Specific examples to be mentioned are o- or m-toluidine, o- or m-anisidine, cresidine, 2,5-dimethylaniline, 2,5-dimethoxyaniline, m-aminoacetanilide, 3-amino-4-methoxyacetanilide, 3-amino-4-methylacetanilide, m-aminophenylurea, N-methylaniline, N-methyl-m-toluidine, N-ethylaniline, N-ethyl-m-toluidine, N-(2-hydroxyethyl)aniline or N-(2-hydroxyethyl)-m-toluidine.

Examples of naphtholsulfonic acids are 1-naphthol-3-sulfonic acid, 1-naphthol-4-sulfonic acid, 1-naphthol-5-sulfonic acid, 1-naphthol-8-sulfonic acid, 1-naphthol-3,6-disulfonic acid, 1-naphthol-3,8-disulfonic acid, 2-naphthol-5-sulfonic acid, 2-naphthol-6-sulfonic acid, 2-naphthol-7-sulfonic acid, 2-naphthol-8-sulfonic acid, 2-naphthol-3,6-disulfonic acid, 2-naphthol-6,8-disulfonic acid, 2-naphthol-3,6,8-trisulfonic acid, 1,8-dihydroxynaphthalene-3,6-disulfonic acid, 2,6-dihydroxynaphthalene-8-sulfonic acid or 2,8-dihydroxynaphthalene-6-sulfonic acid.

Further examples which should be mentioned are 1-naphthylamine, N-phenyl-1-naphthylamine, N-ethyl-1-naphthylamine, N-phenyl-2-naphthylamine, 1-naphthol, 2-naphthol, 1,5-dihydroxynaphthalene, 1,6- dihydroxynaphthalene, 1,7-dihydroxynaphthalene or 2,7-dihydroxynaphthalene.

Examples of aminonaphthalenesulfonic acids are 1-naphthylamine-6-sulfonic acid, 1-naphthylamine-7-sulfonic acid, 1-naphthylamine-8-sulfonic acid, 2-naphthylamine-3,6-disulfonic acid, 2-naphthylamine-5,7-disulfonic acid or 2-naphthylamine-6,8-disulfonic acid.

Examples of aminonaphtholsulfonic acids which should be mentioned are 1-amino-5-hydroxynaphthalene-7-sulfonic acid, 1-amino-8-hydroxynaphthalene-4-sulfonic acid, 1-amino-8-hydroxynaphthalene-2,4-disulfonic acid, 1-amino-8-hydroxynaphthalene- 3,6-disulfonic acid, 1-amino-8-hydroxynaphthalene-4,6-disulfonic acid, 2-amino-5-hydroxy-naphthalene-7-sulfonic acid, 2-amino-8-hydroxynaphthalene-6-sulfonic acid, 2-amino-8-hydroxynaphthalene-3,6-disulfonic acid, 2-amino-5-hydroxynaphthalene-1,7-disulfonic acid, 1-acetylamino-8-hydroxynaphthalene-3,6-disulfonic acid, 1-benzoylamino-8-hydroxynaphthalene-3,6-disulfonic acid, 1-acetylamino-8-hydroxynaphthalene-4,6-disulfonic acid, 1-benzoylamino-8-hydroxynaphthalene-4,6-disulfonic acid, 1-acetylamino-5-hydroxynaphthalene-7-sulfonic acid, 2-methylamino-8-hydroxynaphthalene-6-sulfonic acid or 2-(3-or 4-hydroxysulfonylphenylamino)-8-hydroxynaphthalene-6-sulfonic acid.

Particularly important coupling components are those which have sulfo and/or carboxyl groups and couple in the position ortho or para to a hydroxyl and/or amino group.

Examples of such coupling components which may be mentioned are 2-acetylamino-5-hydroxynaphthalene-7-sulfonic acid, 2-acetylamino-8-hydroxynaphthalene-6-sulfonic acid, 1-acetylamino-8-hydroxynaphthalene-3,6-disulfonic acid, 1-benzoylamino-8-hydroxynaphthalene-3,6-disulfonic acid, 1-acetylamino-8-hydroxynaphthalene-4,6-disulfonic acid or 1-benzoylamino-8-hydroxynaphthalene-4,6-disulfonic acid.

Examples of coupling components of the other series are: pyrazolones, aminopyrazoles, 2,6-diaminopyridines, pyridones, hydroxy- or aminopyrimidines, indoles or N-arylacetoacetamides.

Coupling components of this series without fiber-reactive groups correspond, for example, to the formulae XVIa–f

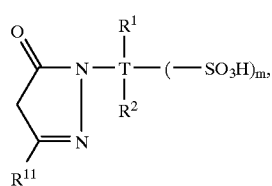 (XVI a)

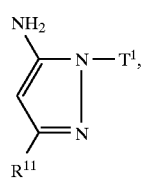 (XVI b)

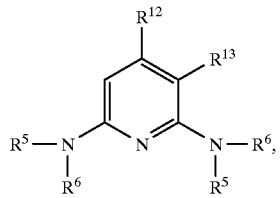 (XVI c)

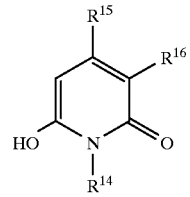 (XVI d)

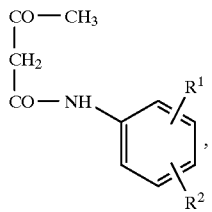 (XVI e)

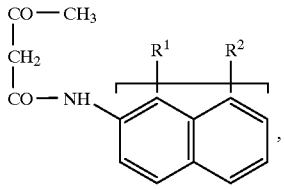 (XVI f)

where

T is the radical of a benzene or naphthalene ring, $T^1$ is $C_1$–$C_4$-alkyl, cyclohexyl, benzyl or phenyl which is substituted once to three times by fluorine, chlorine, bromine, methoxy, nitro, hydroxysulfonyl, carboxyl, acetyl, acetylamino, methylsulfonyl, sulfamoyl or carbamoyl, $R^{11}$ is methyl, carboxyl, $C_1$–$C_4$-alkoxycarbonyl or phenyl, $R^{12}$ is hydrogen or $C_1$–$C_4$-alkyl which can be substituted by methoxy, ethoxy or cyano, $R^{13}$ is hydrogen, methyl, hydroxysulfonylmethyl, hydroxysulfonyl, cyano or carbamoyl, $R^{14}$ is hydrogen, $C_1$–$C_4$-alkyl which can be substituted by phenyl, hydroxysulfonylphenyl, hydroxyl, amino, methoxy, ethoxy, carboxyl, hydroxysulfonyl, acetylamino, benzoylamino or cyano, or cyclohexyl, phenyl which is unsubstituted or substituted by carboxyl, hydroxysulfonyl, benzoylamino, acetylamino, methyl, methoxy, cyano or chlorine, or amino which is substituted by phenyl, $C_1$–$C_4$-alkyl, $C_1$–$C_4$-alkanoyl or benzoyl, $R^{15}$ is $C_1$–$C_4$-alkyl, phenyl, hydroxyl, cyano, acetyl, benzoyl, carboxyl, methoxycarbonyl, carbamoyl or hydroxysulfonylmethyl and $R^{16}$ is hydrogen, chlorine, bromine, acetylamino, amino, nitro, hydroxysulfonyl, sulfamoyl, methylsulfonyl, phenylsulfonyl, carboxyl, $C_1$–$C_4$-alkoxycarbonyl, $C_1$–$C_4$-alkanoyl, benzoyl, carbamoyl, cyano or hydroxysulfonylmethyl, and $R^1$, $R^2$, $R^5$, $R^6$ and m each have the abovementioned meanings.

Examples of pyrazolone coupling components which may be mentioned are 3-methyl-, 3-carboxy- or 3-($C_1$–$C_4$-alkoxycarbonyl)-5-pyrazolones which can carry in position 1 hydrogen, phenyl which is unsubstituted or substituted by methyl, ethyl, fluorine, chlorine, bromine, trifluoromethyl, methoxy, ethoxy, cyano, phenoxy, phenylsulfonyl, methylsulfonyl, hydroxysulfonyl, acetylamino, nitro, hydroxyl, carboxyl, carbamoyl or sulfamoyl, or 1- or 2-naphthyl substituted by hydroxysulfonyl. Examples which should be mentioned are 1-phenyl-, 1-(2-chlorophenyl)-, 1-(2-methoxyphenyl)-, 1-(2-methylphenyl)-, 1-(1,5-dichlorophenyl)-, 1-(2,6-dichlorophenyl)-, 1-(2-methyl-6-chlorophenyl)-, 1-(2-methoxy-5-methylphenyl)-, 1-(2-methoxy-5-hydroxysulfonylphenyl)-, 1-(2,5-dichloro-4-hydroxysulfonylphenyl)-, 1-(2,5-dihydroxysulfonylphenyl)-, 1-(2-carboxyphenyl)-, 1-(3-hydroxysulfonylphenyl)-, 1-(4-hydroxysulfonylphenyl)- or 1-(3-sulfamoylphenyl)-3-carboxyl-5-pyrazolone, 1-(3- or 4-hydroxysulfonylphenyl)-, 1-(2-chloro-4- or -5-hydroxysulfonylphenyl)-, 1-(2-methyl-4-hydroxysulfonylphenyl)-, 1-(2,5-dichlorophenyl)-, 1-(4,8-dihydroxysulfonyl-1-naphthyl)-, 1-(6-hydroxysulfonyl-1-naphthyl)-3-methyl-5-pyrazolone, ethyl 1-phenyl-5-pyrazolone-3-carboxylate, ethyl 5-pyrazolone-3-carboxylate or 5-pyrazolone-3-carboxylic acid.

Further coupling components from the pyrazole series are, for example, 1-methyl-, 1-ethyl-, 1-propyl-, 1-butyl-, 1-cyclohexyl-, 1-benzyl- or 1-phenyl-5-aminopyrazole, 1-(4-chlorophenyl)-, 1-(4-methylphenyl)-5-aminopyrazole or 1-phenyl-3-methyl-5-aminopyrazole.

Acetoacetanilides are, in particular, acetoacetanilide or its derivatives which are substituted one or more times in the phenyl nucleus by chlorine, methyl, ethyl, methoxy, ethoxy, acetylamino, hydroxysulfonyl, carboxyl, carbamoyl or sulfamoyl.

Coupling components derived from pyridine are, for example, the derivatives described in DE-A 2 260 827.

Examples of suitable pyrimidine coupling components are the compounds listed in DE-A-2 202 820, DE-A-2 308 663 or DE-A-3 119 349. Mention should also be made of barbituric acid and its N-substitution products. In this case, particularly suitable N-substituents are $C_1$–$C_4$-alkyl or phenyl.

Examples of indole coupling components which may be mentioned are 2-methylindole, 2-phenylindole, 2-phanylindole-5-sulfonic acid, 1-methyl-2-phenylindole, 1-(2-hydroxyethyl)-, 1-(2-carboxyethyl)-, 1-(2-carbamoylethyl)-2-methyl- or -2-phenylindole.

Examples of pyridone coupling components which may be mentioned are 1-ethyl-2-hydroxy-4-methyl-5-carbamoyl-6-pyridone, 1-(2-hydroxyethyl)-2-hydroxy-4-methyl-5-carbamoyl-6-pyridone, 1-phenyl-2-hydroxy-4-methyl-5-carbamoyl-6-pyridone, 1-ethyl-2-hydroxy-4-methyl-5-cyano-6-pyridone, 1-ethyl-2-hydroxy-4-methyl-5-hydroxysulfonylmethyl-6-pyridone, 1-methyl-2-hydroxy-4-methyl-5-cyano-6-pyridone, 1-methyl-2-hydroxy-5-acetyl-6-pyridone, 1,4-dimethyl-2-hydroxy-5-cyano-6-pyridone, 1,4-dimethyl-5-carbamoyl-6-pyridone, 2,6-dihydroxy-4-ethyl-5-cyanopyridine, 2-hydroxy-4-ethyl-5-carbamoyl-6-pyridone, 1-ethyl-2-hydroxy-4-methyl-5-hydroxysulfonylmethyl-6-pyridone 1-methyl-2-hydroxy-4-methyl-5-methylsulfonyl-6-pyridone or 1-carboxymethyl-2-hydroxy-4-ethyl-5-phenylsulfonyl-6-pyridone.

Examples of coupling components K of the benzene or naphthalene series containing fiber-reactive groups are compounds of the formulae XVIIa–f

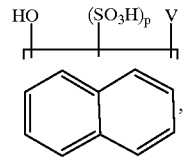

(XVII a)

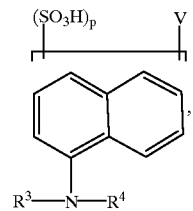

(XVII b)

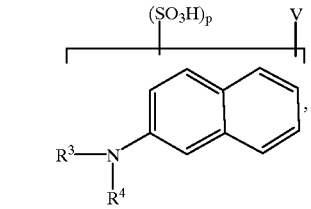

(XVII c)

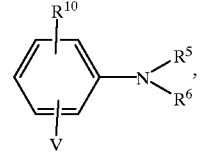

(XVII d)

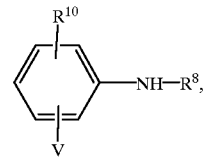

(XVII e)

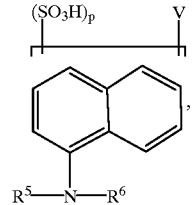

(XVII f)

where $R^3$, $R^4$, $R^5$, $R^6$, $R^8$, $R^{10}$, V and p each have the abovementioned meanings.

Coupling components of the pyrazolone, aminopyrazole, 2,6-diaminopyridine, pyridone, hydroxy- or aminopyrimidine, indole or N-arylacetoacetamide series containing fiber-reactive groups correspond, for example, to the formulae XVIIIa–f (XVIII a)

$$\text{structure with } N-T^2(-SO_3H)_p, R^{2V}, R^{17}$$

(XVIII b)

$$\text{structure with } NH_2, N-T^2(-SO_3H)_p, V, R^{17}$$

(XVIII c)

$$\text{pyridine structure with } R^{12}, R^{13}, R^5-N, N-R^{18}-V, R^6, R^5$$

(XVIII d)

$$\text{structure with } R^{15}, R^{16}, HO, R^{18}-V$$

(XVIII e)

$$\begin{array}{l} CO-CH_3 \\ | \\ CH_2 \quad R^1 \\ | \\ CO-NH \quad R^2 \\ \quad\quad V \end{array}$$

(XVIII f)

$$\begin{array}{l} CO-CH_3 \\ | \\ CH_2 \quad R^1 \quad R^2 \\ | \\ CO-NH \\ \quad\quad\quad V \end{array}$$

where $T^2$ is the radical of a benzene or naphthalene ring, $R^{17}$ is methyl, carboxyl, $C_1$–$C_4$-alkoxycarbonyl or phenyl and $R^{18}$ is $C_1$–$C_6$-alkylene and $R^1$, $R^2$, $R^5$, $R^6$, $R^{12}$, $R^{13}$, $R^{15}$, $R^{16}$, p and V each have the abovementioned meanings.

Pyrazolone coupling components carrying fiber-reactive radicals V are derived, for example, from the following pyrazolones: 1-(3- or 4-aminophenyl)-, 1-(2-hydroxysulfonyl-5-aminophenyl)- or 1-(2-methoxy-5-aminophenyl)-3-carboxy-5-pyrazolone, 1- (3- or 4-aminophenyl)- or 1-(6-amino-4,8-dihydroxysulfonyl-2-naphthyl)-3-carboxy-5-pyrazolone.

In place of the azo dye radicals, the dyes of the formula I can also contain corresponding metal complex azo dye radicals. Suitable complexing metals in this case are, in particular, copper, cobalt, chromium, nickel or iron, with copper, cobalt or chromium being preferred.

In this case, the metallized groups are in each case preferably in the position ortho to the azo group, eg. in the form of o,o'-dihydroxy-, o-hydroxy-o'-carboxy-, o-carboxy-o'-amino- or o-hydroxy-o'-amino-azo groups.

W in formula I is furthermore, for example, the radical of a metallized formazan dye, particular mention being made of copper formazans. Copper formazans are known and are described, for example, in K. Venkataraman "The Chemistry of Synthetic Dyes", Vol. III, Academic Press, New York, London, 1970.

Particularly preferred copper formazan dyes are those of the formula XIX (XIX)

$$\text{copper formazan complex structure with } (E-L^7)_n, (L^7-E)_w, Cu, G^9, G^{10}, G^{11}, cat^\oplus$$

where $cat^\oplus$ is the equivalent of a cation, $G^9$, $G^{10}$ and $G^{11}$ are identical or different and are each, independently of one another, hydrogen or hydroxysulfonyl, n is 0 or 1 and w is 0 or 1, and E and $L^7$ each have the abovementioned meanings, with the proviso that n and w are not both 0.

In formula XIX, $cat^\oplus$ is the equivalent of a cation. It is either a proton or is derived from metal or ammonium ions. Metal ions are in particular lithium, sodium or potassium ions. For the purpose of the invention, ammonium ions mean unsubstituted or substituted ammonium cations. Examples of substituted ammonium cations are monoalkyl-, dialkyl-, trialkyl-, tetraalkyl- or benzyltrialkylammonium cations or cations derived from nitrogen-containing five- or six-membered saturated heterocycles, such as pyrrolidinium, piperidinium, morpholinium or piperazinium cations or their N-monoalkyl- or N,N-dialkyl-substituted products. In this connection, alkyl generally means straight-chain or branched $C_1$–$C_{20}$-alkyl, which can be substituted by 1 or 2 hydroxyl groups and/or interrupted by 1 to 4 oxygen atoms in ether functionality.

Cations to be particularly emphasized are protons or lithium, sodium or potassium ions, and said metal cations are also preferred cations when the reactive dyes XIX are in salt form.

A method for preparing the formazans on which these dyes are based is described, for example in EP-A-315 046.

W in formula I is, furthermore, for example the radical of an anthraquinone dye. Anthraquinones are known and are described, for example, in K. Venkataraman "The Chemistry of Synthetic Dyes", Vol. II, Academic Press, New York, 1952.

Particularly preferred anthraquinone dyes are those of the formula XX

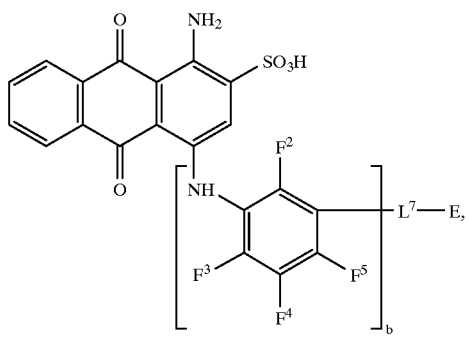

where E and $L^7$ each have the abovementioned meanings, b is 0 or 1, and $F^2$ and $F^3$ are each, independently of one another, hydrogen or methyl and one of the two radicals $F^4$ and $F^5$ is hydrogen or methyl and the other is hydroxysulfonyl.

W in formula I is, furthermore, for example the radical of a triphendioxazine dye. Triphendioxazines are known and are described, for example, in EP-A 141 359 or EP-A 311 969.

Particularly preferred triphendioxazine dyes are those of the formula XXI

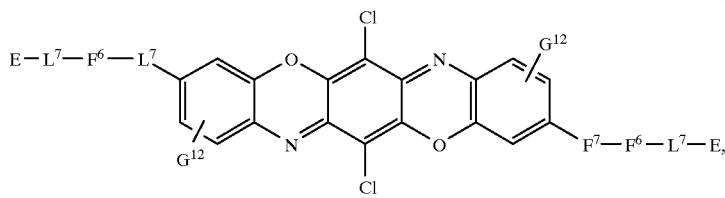

where

E and $L^7$ each have the abovementioned meanings, and $G^{12}$ is hydroxysulfonyl or the radical $SO_2$—$C_2H_4$—$SO_3H$, $F^7$ is oxygen, imino or $C_1$–$C_4$-alkylimino and $F^6$ is $C_2$–$C_4$-alkylene or phenylene.

W in formula I is furthermore, for example, the radical of a metallized phthalocyanine dye. Phthalocyanines are known and are described, for example, in F. H. Moser, D. L. Thomas "The Phthalocyanines", Vol. II, CRC Press, Boca Raton, Fla., 1983.

Particularly preferred phthalocyanine dyes are those of the formula XXII

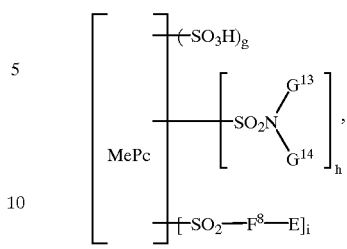

where

Pc is the phthalocyanine radical, $G^{13}$ and $G^{14}$ are each, independently of one another, hydrogen or $C_1$–$C_4$-alkyl, $F^8$ is imino or $C_1$–$C_4$-alkylimino, Me is copper or nickel, g is 0, 1 or 2, h is 0, 1 or 2 and i is 1 or 2, and E has the abovementioned meanings.

The novel reaction dyes of the formula I can be prepared by conventional methods.

For example, a suitable dye of the formula XXIII $$W^1\text{—}G^{15}, \quad\quad\quad (XXIII)$$

where $W^1$ is the radical of a chromophore which may have further reactive groups and is derived from a mono- or disazo dye which may be metallized, a triphendioxazine, an anthraquinone, a metallized formazan or a metallized phthalocyanine, and $G^{15}$ is a radical of the formula $NHZ^3$, COHal or $SO_2$Hal where $Z^3$ and Hal each have the abovementioned meanings, can be reacted with a fiber-reactive compound of the formula XXIV $$G^{15}\text{—}E, \quad\quad\quad (XXIV)$$

where $G^{15}$ and E each have the abovementioned meanings.

When $L^1$ (case 1) is a urea bridge or a triazine radical, synthetic steps customary for these classes of substances are inserted.

It is also possible to start from intermediates of compounds of the formula XXIII which do not yet have a chromophore radical and first to react these with the fiber-reactive compound XXIV and then to assemble the chromophore radical $W^1$.

When the radical W is a coupling component, the dyes according to the invention are obtained by, for example, diazotizing the fiber-reactive compound of the formula XXV $$H_2N\text{—}E, \quad\quad\quad (XXV)$$

where E has the abovementioned meaning, in a conventional way and coupling to a coupling component of the formula XXVI $W^2$—H     (XXVI)

where $W^2$ is the radical of a coupling component to which the radical of a diazo component may additionally be linked via an azo bridge and which may have additional reactive groups.

When b in formula I has the value 1, the doubled chromophores can be obtained, for example, by either doubling the finished individual chromophores or else initially doubling suitable intermediates and then assembling the particular chromophore systems.

The preparation of the fiber-reactive compounds of the formulae XXIV and XXV is known and is described, for example, in EP-A 680 951.

The present invention further relates to sulfur compounds of the formula XXVII

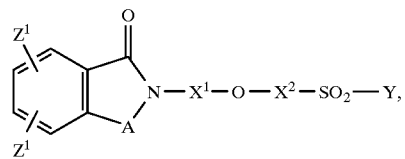     (XXVII)

where the $Z^1$ radicals are each, independently of one another, hydrogen, $C_1$–$C_6$-alkyl, $C_1$–$C_6$-alkoxy, halogen, nitro, amino, hydroxysulfonyl, $C_1$–$C_6$-alkoxycarbonyl, carbamoyl or $C_1$–$C_6$-mono- or dialkylcarbamoyl, A is methylene, carbonyl, sulfonyl or a radical of the formula $CH_2$—CO or $CH_2$—$SO_2$ where the methylene group is linked in each case to the benzene ring, $X^1$ and $X^2$ are each, independently of one another, $C_2$–$C_4$-alkylene and Y is vinyl or a radical of the formula $C_2H_4OH$ or $C_2H_4Q$, where Q is a group which can be eliminated under alkaline conditions.

Preferred sulfur compounds of the formula XXVII are those where A is methylene, carbonyl or the radical of the formula $CH_2$—CO.

Further preferred sulfur compounds of the formula XXVII are those where $X^1$ and $X^2$ are each $C_2$- or $C_3$-alkylene, in particular each $C_2$-alkylene.

Further preferred sulfur compounds of the formula XXVII are those where one radical $Z^1$ is hydrogen or amino and the other is hydrogen.

Particularly preferred sulfur compounds of the formula XXVII are those where one radical $Z^1$ is amino and the other is hydrogen.

Further particularly preferred sulfur compounds of the formula XXVII are those where A is methylene.

The novel sulfur compounds of the formula XXVII can be obtained in a conventional way. For example, a benzene derivative of the formula XXVIII

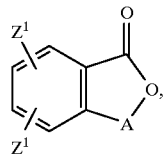     (XXVIII)

where $Z^1$ and A each have the abovementioned meanings, can be reacted with an amine of the formula XXIX

     (XXIX)

where $X^1$ and $X^2$ and Y each have the abovementioned meanings.

It is advantageous initially to react the benzene derivatives of the formula XXVIII with a thioether of the formula XXIXa

     (XXIXa)

where $X^1$, $X^2$ and Y each have the abovementioned meanings, and subsequently to oxidize the sulfide to the sulfonyl group, eg. with hydrogen peroxide.

The $Z^1$ radicals can, when they differ from hydrogen, also be introduced subsequently into the benzene ring in a conventional way. This is the preferred route in particular for introduction of the hydroxysulfonyl group or the nitro group, which can subsequently be reduced to the amino group.

The novel sulfur compounds of the formula XXVII are valuable intermediates for preparing dyes, especially the reactive dyes defined herein.

The novel reactive dyes of the formula I are advantageously suitable for dyeing or printing organic substrates having hydroxyl groups or nitrogen atoms. Examples of such substrates are leather or fiber material which predominantly comprises natural or synthetic polyamides or natural or regenerated cellulose. The novel dyes are preferably suitable for dyeing and printing textile material based on wool or, in particular, cotton.

Intense dyeings with very high fixation yields are obtained in particular on cellulose-based substrates, and these have very good light fastness and excellent wet fastness properties such as washing, chlorine bleach, peroxide bleach, alkali, sea water or sweat fastness properties.

The following examples are intended to explain the invention in detail.

EXAMPLE 1 a) 94 g of cyanuric chloride were dispersed in a mixture of 400 ml of ice-water, 1 ml of 30% by weight hydrochloric acid and 0.5 g of a dispersant and, at 0–5° C., a solution of 126 g of aniline-2,5-disulfonic acid in 250 ml of water and 35 ml of 50% by weight sodium hydroxide solution were added. After stirring at 0–5° C. and pH 4–5, which was maintained with 47 g of sodium bicarbonate, for 4 hours, the reaction was complete and the mixture was filtered to clarify.

A solution of 170 g of 1-amino-8-hydroxynaphthalene-3,6-disulfonic acid (monosodium salt) in 500 ml of water and 25 ml of 50% by weight sodium hydroxide solution were run into the filtrate while maintaining the pH at 4.5–5 with sodium bicarbonate without further cooling. After stirring at room temperature overnight, the condensate was precipitated with 600 g of sodium chloride, filtered off with suction, washed with 20% by weight brine and dried at 50° C. under reduced pressure.

b) 18.2 g of the anchor compound of the formula

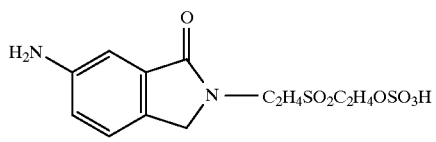

were dissolved in 200 ml of water with 4 g of sodium bicarbonate at pH 4.4. After cooling with 150 g of ice, 18 ml of 30% by weight hydrochloric acid were added, and diazotization was carried out by dropwise addition of 15 ml of 3.33 N aqueous sodium nitrite solution. After stirring at 0–5° C. for 30 minutes, a slight excess of nitrite was removed with sulfamic acid, and a solution of 52 g of the compound described in a) (purity: 95%; sodium chloride content: 20%) in 200 ml of water was added to the mixture. Coupling took place by dropwise addition of an aqueous sodium acetate solution until the pH was 5.

Precipitation with 200 g of potassium chloride, filtration with suction and drying resulted in the dye of the formula

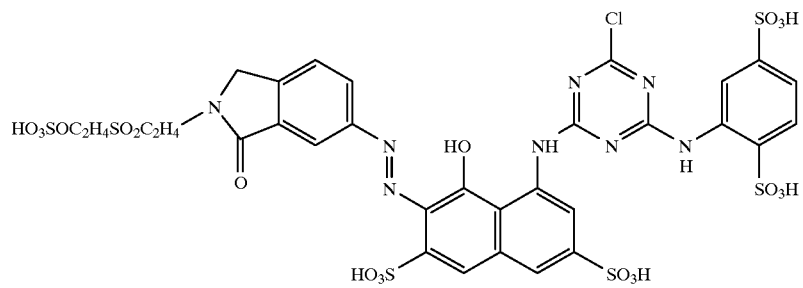

being isolated as pentasodium salt. It dyes cotton either by the exhaust process at 40–60° C. or by the cold pad-batch process at room temperature in bluish red hues. The dyeings are distinguished by very good general use fastness properties and high degrees of fixation and are very insensitive to fluctuations in the dyeing temperature.

The dyes listed in following Table 1 can be obtained in a similar way.

TABLE 1

| Ex. No. | $Y^1$ | X | K | Hal | Ar | Hue |
|---|---|---|---|---|---|---|
| 2 | $(CH_2)_2OSO_3H$ | $(CH_2)_2$ | [naphthalene with HO, NH, CH₃, HO₃S, SO₃H] | Cl | [benzene with SO₃H, NH, SO₃H] | bluish red |
| 3 | $(CH_2)_2OSO_3H$ | $(CH_2)_2$ | [naphthalene with HO, NH, CH₃, HO₃S, SO₃H] | Cl | [benzene with SO₃H, NH] | bluish red |

TABLE 1-continued
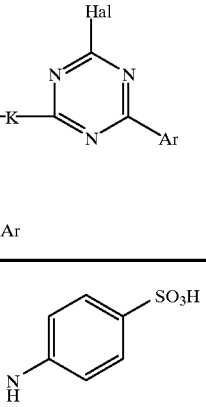
| Ex. No. | Y₁ | X | K | Hal | Ar | Hue |
|---|---|---|---|---|---|---|
| 4 | (CH₂)₂OSO₃H | (CH₂)₂ | 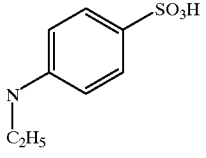 | Cl | 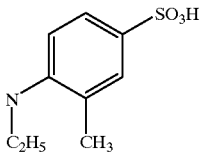 | bluish red |
| 5 | (CH₂)₂OSO₃H | (CH₂)₂ | 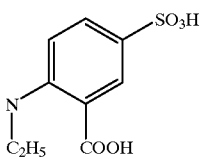 | Cl | 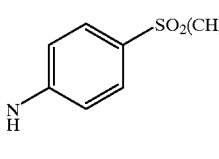 | bluish red |
| 6 | (CH₂)₂OSO₃H | (CH₂)₂ | 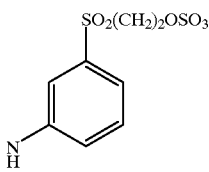 | Cl | | bluish red |
| 7 | (CH₂)₂OSO₃H | (CH₂)₂ | | Cl | | bluish red |
| 8 | (CH₂)₂OSO₃H | (CH₂)₂ | | Cl | | bluish red |
| 9 | (CH₂)₂OSO₃H | (CH₂)₂ | | Cl | | bluish red |

TABLE 1-continued
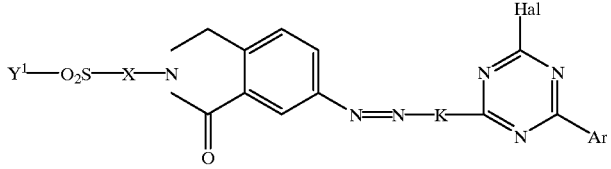
| Ex. No. | Y₁ | X | K | Hal | Ar | Hue |
|---|---|---|---|---|---|---|
| 10 | (CH₂)₂OSO₃H | (CH₂)₂ | 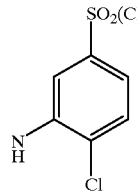 | Cl | SO₂(CH₂)₂OSO₃H, NH, Cl (chlorophenyl) | bluish red |
| 11 | (CH₂)₂OSO₃H | (CH₂)₂ | 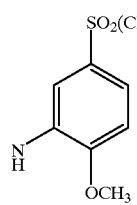 | Cl | SO₂(CH₂)₂OSO₃H, NH, OCH₃ | bluish red |
| 12 | (CH₂)₂OSO₃H | (CH₂)₂ | 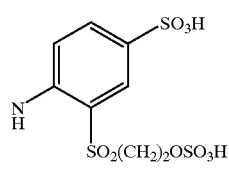 | Cl | SO₃H, NH, SO₂(CH₂)₂OSO₃H | bluish red |
| 13 | (CH₂)₂Cl | (CH₂)₂ | 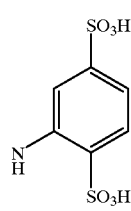 | Cl | SO₃H, NH, SO₃H | bluish red |
| 14 | (CH₂)₂Cl | (CH₂)₂ | 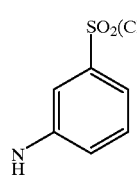 | Cl | SO₂(CH₂)₂Cl, NH | bluish red |
| 15 | CH=CH₂ | (CH₂)₂ | 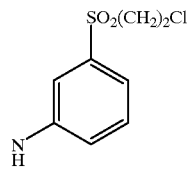 | Cl | SO₂(CH₂)₂Cl, NH | bluish red |

TABLE 1-continued

[Structure: Y¹—O₂S—X—N(H)—C(=O)—[4-ethylphenyl]—N=N—K—[triazine with Hal, Ar substituents]]

| Ex. No. | Y₁ | X | K | Hal | Ar | Hue |
|---|---|---|---|---|---|---|
| 16 | CH=CH₂ | (CH₂)₂ | 8-amino-1-hydroxy-7-methyl-3,6-disulfonaphthalene | Cl | 2,5-disulfo-aniline | bluish red |
| 17 | (CH₂)₂SSO₃H | (CH₂)₂ | 8-amino-1-hydroxy-7-methyl-3,6-disulfonaphthalene | Cl | 2,5-disulfo-aniline | bluish red |
| 18 | (CH₂)₂OSO₃H | (CH₂)₂ | 8-amino-1-hydroxy-7-methyl-3,6-disulfonaphthalene | F | 3-sulfo-aniline | bluish red |
| 19 | (CH₂)₂OSO₃H | (CH₂)₂ | 8-amino-1-hydroxy-7-methyl-3,6-disulfonaphthalene | Cl | 2,5-disulfo-4-(SO₂(CH₂)₂OSO₃H)-aniline | bluish red |
| 20 | (CH₂)₂OSO₃H | (CH₂)₂ | 6-amino-1-hydroxy-2-methyl-3-sulfonaphthalene | Cl | 2,5-disulfo-aniline | orange |
| 21 | (CH₂)₂OSO₃H | (CH₂)₂ | 6-amino-1-hydroxy-2-methyl-3-sulfonaphthalene | Cl | 2,5-disulfo-aniline | orange |

TABLE 1-continued
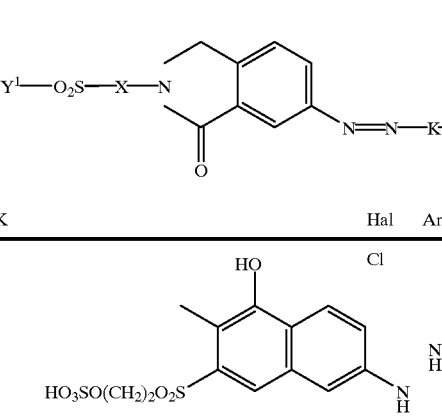
| Ex. No. | Y₁ | X | K | Hal | Ar | Hue |
|---|---|---|---|---|---|---|
| 22 | (CH₂)₂OSO₃H | (CH₂)₂ | 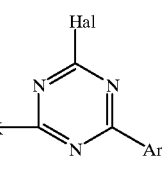 | Cl | 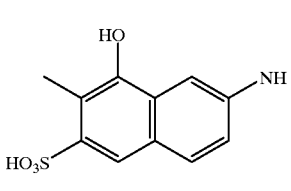 | reddish orange |
| 23 | (CH₂)₂OSO₃H | (CH₂)₂ | 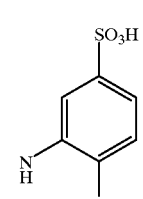 | Cl | 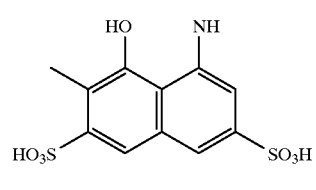 | reddish orange |
| 24 | (CH₂)₂OSO₃H | (CH₂)₃ | 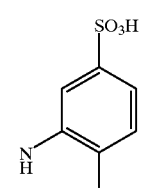 | Cl | 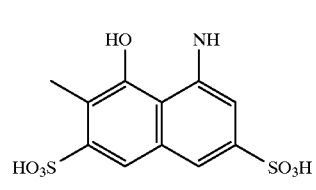 | bluish red |
| 25 | (CH₂)₂OSO₃H | (CH₂)₂O(CH₂)₂ | 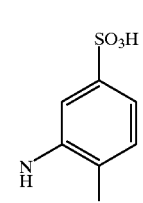 | Cl | 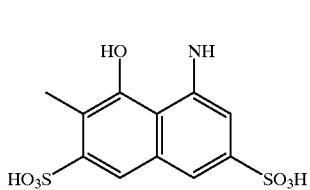 | bluish red |
| 26 | (CH₂)₂OSO₃H | (CH₂)₃ | 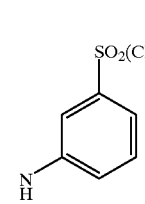 | Cl | 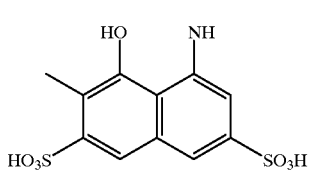 | bluish red |
| 27 | (CH₂)₂OSO₃H | (CH₂)₂O(CH₂)₂ | 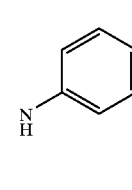 | Cl | | bluish red |

EXAMPLE 28

The anchor compound described in Example 1b) was coupled under the conditions given therein to N-acetyl H acid which had previously been prepared from H acid and acetic anhydride in aqueous solution.

The dye of the formula

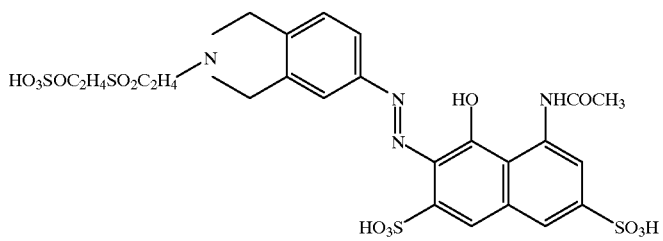

obtained by salting out with sodium chloride dyes cotton in a bluish red, clear hue with a good fastness profile.

The dyes listed in following Table 2 have comparable properties.

TABLE 2

| Ex. No. | Ac | X |
|---|---|---|
| 29 | COC$_6$H$_5$ | (CH$_2$)$_2$ |
| 30 | 3,5-dichlorophenyl | (CH$_2$)$_2$ |
| 31 | COC$_2$H$_5$ | (CH$_2$)$_2$ |
| 32 | CO(CH$_2$)$_2$COOH | (CH$_2$)$_2$ |
| 33 | CO(CH$_2$)$_2$SO$_3$H | (CH$_2$)$_2$ |
| 34 | CONH—C$_6$H$_5$ | (CH$_2$)$_2$ |
| 35 | CONH—(CH$_2$)$_2$—C$_6$H$_4$—SO$_3$H | (CH$_2$)$_2$ |
| 36 | COC$_6$H$_5$ | (CH$_2$)$_3$ |
| 37 | 3,5-dichlorophenyl | (CH$_2$)$_3$ |
| 38 | COC$_2$H$_5$ | (CH$_2$)$_3$ |
| 39 | CO(CH$_2$)$_2$COOH | (CH$_2$)$_3$ |
| 40 | CO(CH$_2$)$_2$SO$_3$H | (CH$_2$)$_3$ |
| 41 | CONH—C$_6$H$_5$ | (CH$_2$)$_3$ |
| 42 | CONH—(CH$_2$)$_2$—C$_6$H$_4$—SO$_3$H | (CH$_2$)$_3$ |
| 43 | COC$_6$H$_5$ | (CH$_2$)$_2$O(CH$_2$)$_2$ |
| 44 | 3,5-dichlorophenyl | (CH$_2$)$_2$O(CH$_2$)$_2$ |
| 45 | COC$_2$H$_5$ | (CH$_2$)$_2$O(CH$_2$)$_2$ |
| 46 | CO(CH$_2$)$_2$COOH | (CH$_2$)$_2$O(CH$_2$)$_2$ |
| 47 | CO(CH$_2$)$_2$SO$_3$H | (CH$_2$)$_2$O(CH$_2$)$_2$ |
| 48 | CONH—C$_6$H$_5$ | (CH$_2$)$_2$O(CH$_2$)$_2$ |
| 49 | CONH—(CH$_2$)$_2$—C$_6$H$_4$—SO$_3$H | (CH$_2$)$_2$O(CH$_2$)$_2$ |
| 50 | COCH$_3$ | (CH$_2$)$_3$ |
| 51 | COCH$_3$ | (CH$_2$)$_2$O(CH$_2$)$_2$ |

EXAMPLE NO. 52 a) 18.5 g of cyanuric chloride were dispersed in 60 ml of a mixture of 60 ml of ice-water, 1 ml of 30% by weight hydrochloric acid and 0.5 g of a dispersant. Addition of a solution of 26.3 g of H acid disodium salt in water which contained 1 g of disodium phosphate at 5–10° C. resulted in complete reaction in the strongly acidic pH range. A solution of 37.5 g of the compound of the formula

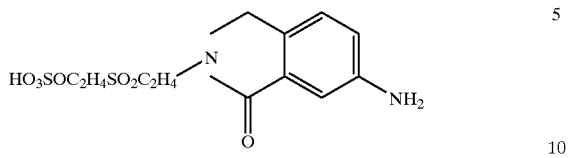

in 200 ml of water and 80 ml of 10% by weight aqueous sodium bicarbonate solution were added to the resulting reaction mixture, and it was then stirred at room temperature while maintaining the pH at 5 overnight.

The reaction product of the formula

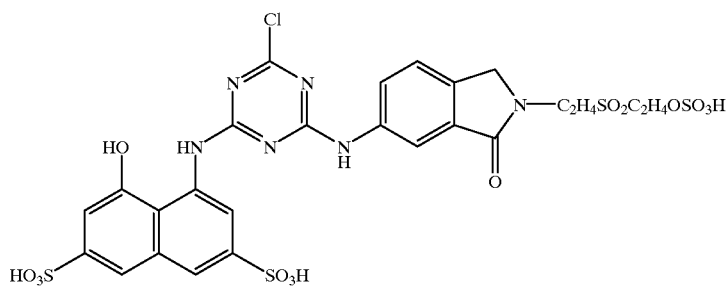

was precipitated with 200 g of sodium chloride, filtered off with suction and washed with 20% by weight brine.

b) 17 g of 2-aminonaphthalene-1,5-disulfonic acid were stirred in a mixture of 50 ml of water, 6 ml of 30% by weight hydrochloric acid and 50 g of ice, and 16.5 ml of 3.33 N aqueous sodium nitrite solution were added. After stirring at 5–10° C. for one hour, the small excess of nitrous acid was destroyed with sulfamic acid, and the entire reaction mixture was mixed with half the solution of the monochlorotriazine described under a) in 350 ml of water. The pH was maintained at 7–8 by adding sodium bicarbonate at 15–20° C. until the reaction was complete. The dye of the formula

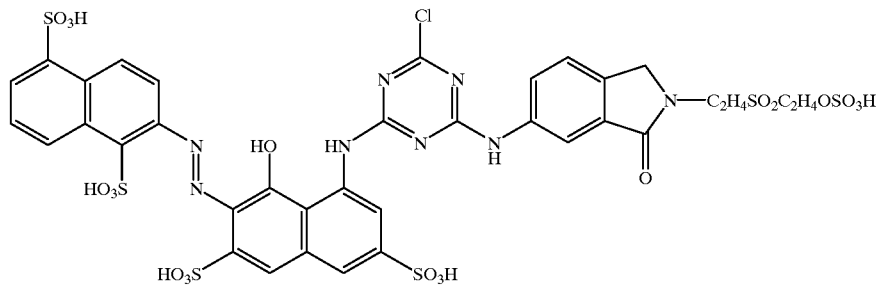

was precipitated with 250 g of potassium chloride and filtered off with suction. It dyes cotton from an alkaline bath in a clear bluish red shade with very good general use fastness properties.

The dyes listed in following Table 3 were obtained in a similar way.

TABLE 3

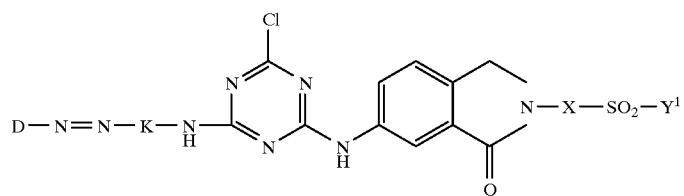

| Ex. No. | D | K | X | Y[1] | Hue |
|---|---|---|---|---|---|
| 53 | 2-methylbenzenesulfonic acid (SO3H ortho to CH3) | 8-amino-1-hydroxy-2-methyl-3,6-disulfo-naphthalene | (CH2)2 | (CH2)2OSO3H | red |
| 54 | 2-methyl-1,4-benzenedisulfonic acid | 8-amino-1-hydroxy-2-methyl-3,6-disulfo-naphthalene | (CH2)2 | (CH2)2OSO3H | yellowish red |
| 55 | 2,4-dimethylbenzenesulfonic acid | 8-amino-1-hydroxy-2-methyl-3,6-disulfo-naphthalene | (CH2)2 | (CH2)2OSO3H | bluish red |
| 56 | 4-methoxy-2-methylbenzenesulfonic acid | 8-amino-1-hydroxy-2-methyl-3,6-disulfo-naphthalene | (CH2)2 | (CH2)2OSO3H | dull bluish red |
| 57 | 3-methyl-2,7-naphthalenedisulfonic acid | 8-amino-1-hydroxy-2-methyl-3,6-disulfo-naphthalene | (CH2)2 | (CH2)2OSO3H | red |
| 58 | 3-methyl-2,5,7-naphthalenetrisulfonic acid | 8-amino-1-hydroxy-2-methyl-3,6-disulfo-naphthalene | (CH2)2 | (CH2)2OSO3H | bluish red |
| 59 | HO3SOC2H4SO2C2H4—N(acyl)-(4-methyl-benzyl) | 8-amino-1-hydroxy-2-methyl-3,6-disulfo-naphthalene | (CH2)2 | (CH2)2OSO3H | red |

TABLE 3-continued

Structure: D—N=N—K—NH—[chlorotriazine]—NH—[ethylphenyl-C(O)—N]—X—SO₂—Y¹

| Ex. No. | D | K | X | Y¹ | Hue |
|---|---|---|---|---|---|
| 60 | HO₃SOC₂H₄SO₂—NH—(4-methylphenyl) | 8-amino-1-hydroxy-2-methyl-naphthalene-3,6-disulfonic acid | (CH₂)₂ | (CH₂)₂OSO₃H | bluish red |
| 61 | HO₃SOC₂H₄SO₂—NH—(3-methylphenyl) | 8-amino-1-hydroxy-2-methyl-naphthalene-3,6-disulfonic acid | (CH₂)₂ | (CH₂)₂OSO₃H | red |
| 62 | HO₃SOC₂H₄SO₂—NH—(4-methylphenyl) | 8-amino-1-hydroxy-2-methyl-naphthalene-3,5-disulfonic acid | (CH₂)₂ | (CH₂)₂OSO₃H | red |
| 63 | 2-methyl-naphthalene-1,5-disulfonic acid | 8-amino-1-hydroxy-2-methyl-naphthalene-3,6-disulfonic acid | (CH₂)₃ | (CH₂)₂OSO₃H | bluish red |
| 64 | 2-methyl-benzene-1,4-disulfonic acid | 8-amino-1-hydroxy-2-methyl-naphthalene-3,6-disulfonic acid | (CH₂)₃ | (CH₂)₂Cl | yellowish red |
| 65 | 2-methyl-benzene-1,4-disulfonic acid | 6-amino-1-hydroxy-2-methyl-naphthalene-3-sulfonic acid | (CH₂)₂ | (CH₂)₂OSO₃H | orange |
| 66 | 2-methyl-naphthalene-1,5-disulfonic acid | 6-amino-1-hydroxy-2-methyl-naphthalene-3-sulfonic acid | (CH₂)₂ | (CH₂)₂OSO₃H | reddish orange |

TABLE 3-continued

General structure:

D—N=N—K—NH—[6-chloro-1,3,5-triazin-2,4-diyl]—NH—[2-ethylphenyl-5-yl with C(=O)N—X—SO₂—Y¹]

| Ex. No. | D | K | X | Y¹ | Hue |
|---|---|---|---|---|---|
| 67 | 2-methylphenyl-SO₂C₂H₄OSO₃H | H acid (1-hydroxy-8-amino-3,6-disulfo-2-methyl-naphthalene) | (CH₂)₂ | (CH₂)₂OSO₃H | red |
| 68 | 4-methylphenyl with phthalimide-N—C₂H₄SO₂C₂H₄OSO₃H | H acid (2-methyl) | (CH₂)₂ | (CH₂)₂OSO₃H | red |
| 69 | 4-methylphenyl with phthalimide-N—C₃H₆SO₂C₂H₄OSO₃H | H acid (2-methyl) | (CH₂)₂ | (CH₂)₂OSO₃H | red |
| 70 | 2-methylnaphthalene-1,5-disulfonic acid | H acid (2-methyl) | (CH₂)₂O(CH₂)₂ | (CH₂)₂OSO₃H | bluish red |
| 71 | 3-methylphenyl-SO₂C₂H₄OSO₃H | H acid (2-methyl) | (CH₂)₃ | (CH₂)₂OSO₃H | bluish red |

EXAMPLE 72 a) 30.3 g of 4-(2-sulfatoethylsulfonyl)aniline sodium salt were dissolved in 500 ml of ice-water, and 30 ml of 3.33 N aqueous sodium nitrite solution were added. Diazotization was carried out by adding 30 ml of 30% by weight hydrochloric acid and then stirring at 0–5° C. for one hour. After excess nitrous acid had been destroyed with sulfamic acid, the resulting dispersion of the diazonium salt was mixed with a solution of 1-(4,6-dichloro-1,3,5-triazin-2-yl)-amino-8-hydroxynaphthalene-4,6-disulfonic acid which was prepared as follows:

A solution of 36.6 g of K acid disodium salt and 25 g of sodium formate in 150 ml of water was run into a vigorously stirred ice-cold dispersion of 18.5 q of cyanuric chloride, 0.1 g of a dispersant, 1 ml of 30% by weight hydrochloric acid and 200 ml of ice-water, and the mixture was then stirred at 5–10° C. and pH 1 for 2 h until the reaction was complete.

The coupling reaction was completed by buffering with sodium acetate solution (pH about 3) and then stirring at 10–15° C. for 30 minutes.

34.1 g of H acid monosodium salt were then added to the dispersion of the dichlorotriazinylazo dye obtained in this way, and the pH was adjusted to 5–5.5 by scattering sodium bicarbonate in, during which the temperature rose to 20° C. After stirring at 20–25° C. while maintaining the above pH for two hours, the reaction was complete and the dye of the formula

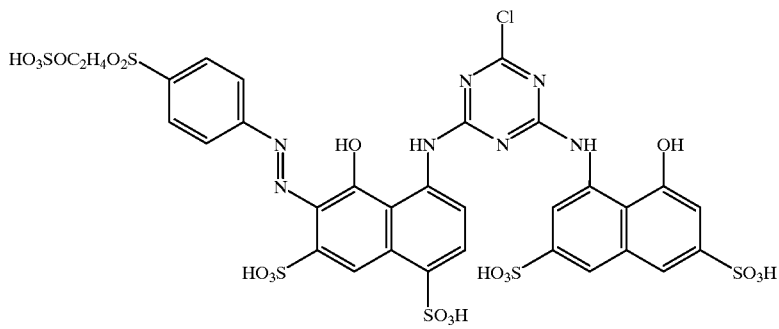

was completely precipitated using potassium chloride and was filtered off with suction and washed with 5% by weight aqueous potassium chloride solution.

b) 0.05 mol of the dye described in a) was mixed with the anchor compound described in Example 1b). Buffering with sodium acetate to a pH of 5 completed the coupling reaction. The dye of the formula

EXAMPLE 73

The sulfatoethylsulfonylaniline used in Example 72a) was replaced by an equivalent amount of the anchor compound described in Example 1b), and the procedure of Example 72b) was then carried out. This resulted in the dye of the formula

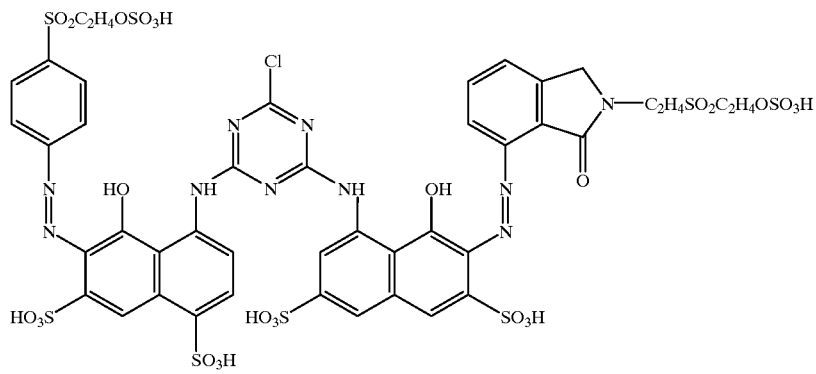

was precipitated with 150 g of potassium chloride, filtered off with suction, washed with 20% by weight aqueous potassium chloride solution and dried at 40° C. under reduced pressure.

The dye dyes cotton equally by the hot exhaust and cold pad-batch processes in clear, neutral red hues with very high color strength and a very high degree of fixation with great insensitivity to temperature variations.

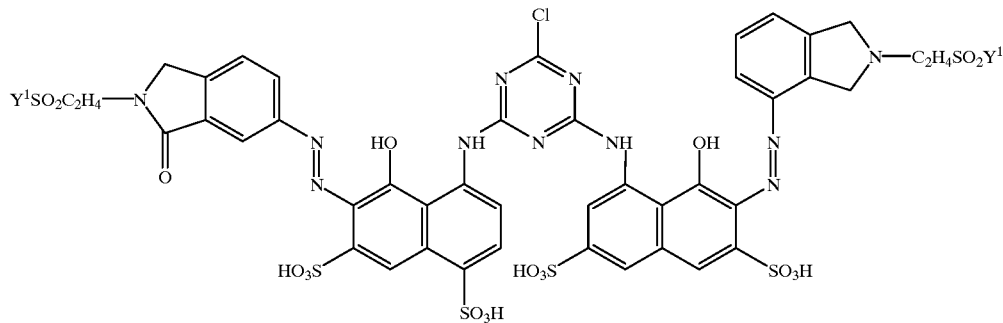

$(Y^1 = C_2H_4OSO_3H)$

The following dyes were obtained in a similar way to Examples 72 and 73, with $Y_1$ being in each case the radical $C_2H_4OSO_3H$.
EXAMPLE 74
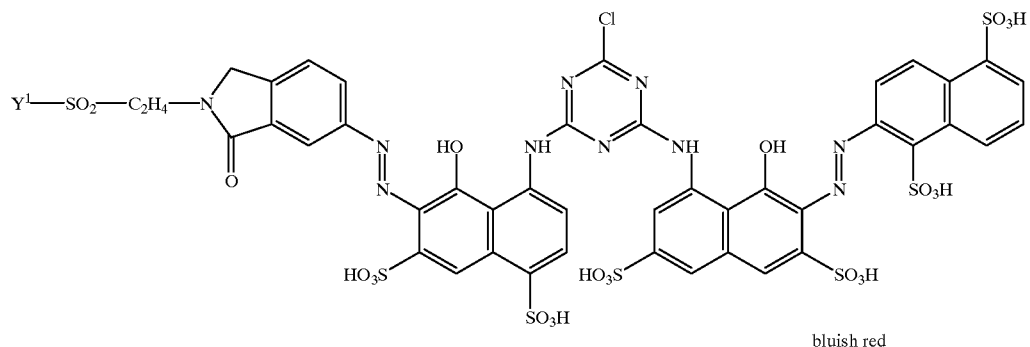
bluish red
EXAMPLE 75
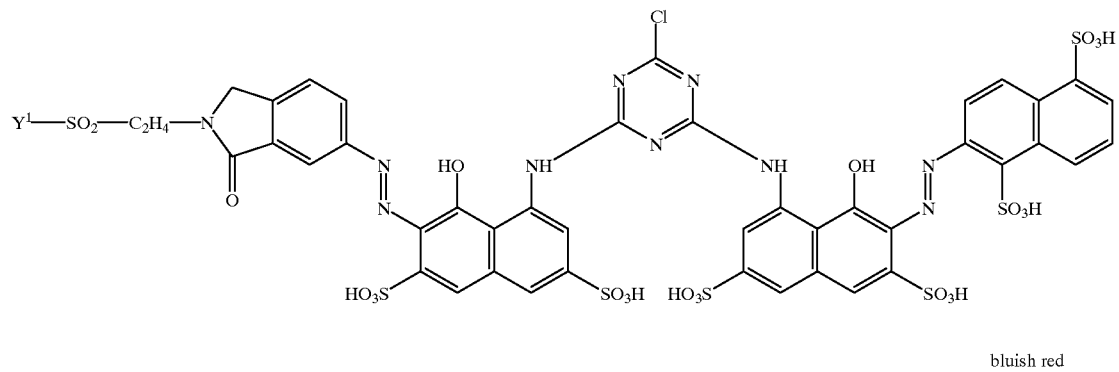
bluish red
EXAMPLE 76
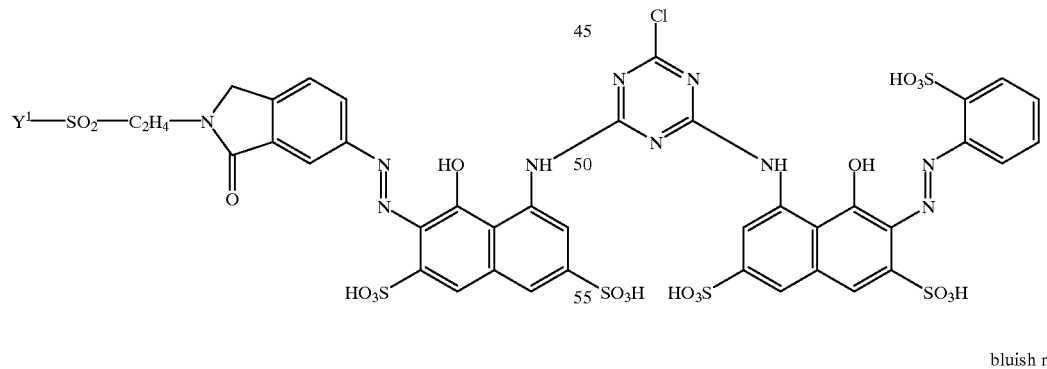
bluish red

EXAMPLE 77

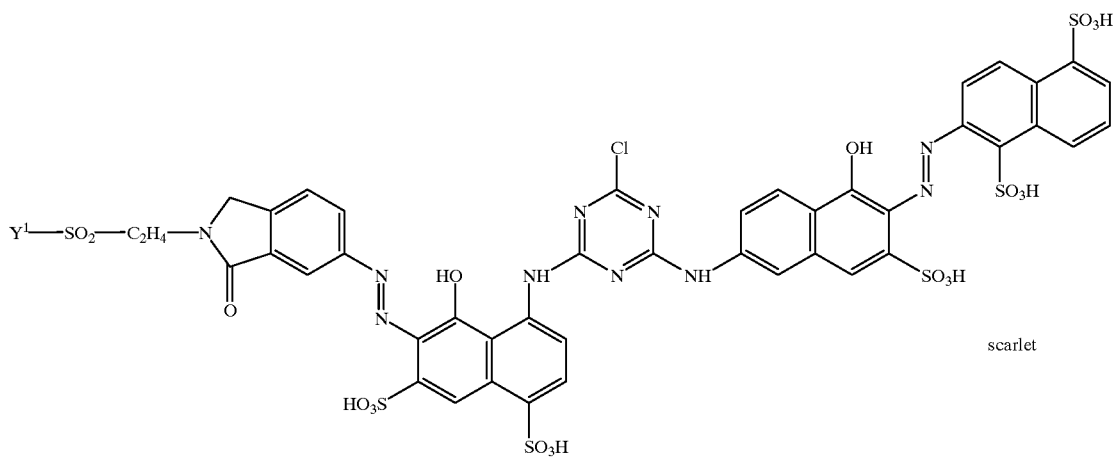

scarlet

EXAMPLE 78

The anchor compound described under 1b) was mixed with a dispersion of 16.5 g of H acid monosodium salt in 150 ml of water and stirred at room temperature overnight.

The monoazo dye which was formed was mixed with another equivalent of the anchor compound described in Example 1b) and coupled with sodium acetate at pH 5. The dye of the formula was precipitated as potassium salt, filtered off with suction, washed with 70% by weight aqueous ethanol and dried at up to 40° C. under reduced pressure.

It dyes cotton in neutral navy and black hues substantially independent of the dyeing processes and temperatures used.

The dyes listed in the following Table 4 are obtained in a similar way.

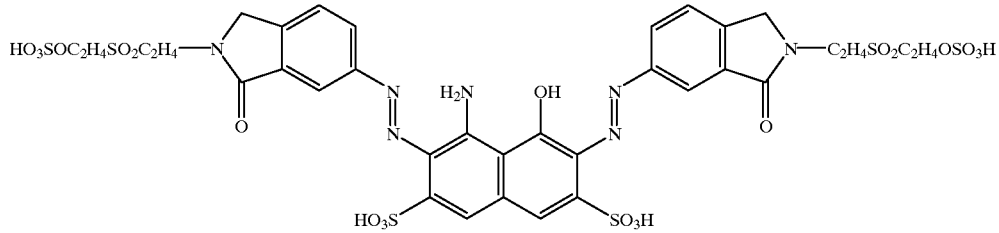

TABLE 4

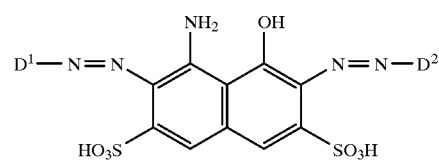

| Ex. No. | $D^1$ | $D^2$ |
|---|---|---|
| 79 | 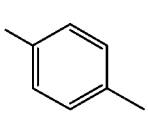 | 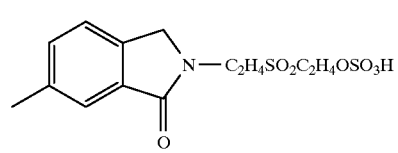 |

TABLE 4-continued

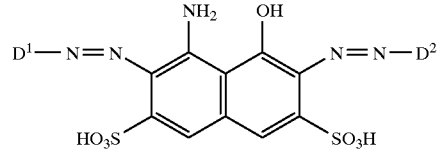

| Ex. No. | D¹ | D² |
|---|---|---|
| 80 | HO₃SOC₂H₄O₂S—(p-tolyl) | 5-methyl-isoindolin-1-one-2-yl—C₂H₄SO₂CH=CH₂ |
| 81 | HO₃SOC₂H₄O₂S—(4-methyl-2-sulfophenyl, SO₃H) | 5-methyl-isoindolin-1-one-2-yl—C₂H₄SO₂CH=CH₂ |
| 82 | 5-methyl-isoindolin-1-one-2-yl—C₂H₄SO₂C₂H₄Cl | 5-methyl-isoindolin-1-one-2-yl—C₂H₄SO₂C₂H₄OSO₃H |
| 83 | 5-methyl-isoindolin-1-one-2-yl—C₃H₆SO₂C₂H₄OSO₃H | 5-methyl-isoindolin-1-one-2-yl—C₃H₆SO₂C₂H₄OSO₃H |
| 84 | HO₃SOC₂H₄O₂S—(p-tolyl) | 5-methyl-isoindolin-1-one-2-yl—C₃H₆SO₂CH=CH₂ |
| 85 | HO₃OC₂H₄O₂S—(p-tolyl) | 5-methyl-isoindolin-1-one-2-yl—C₂H₄OC₂H₄SO₂C₂H₄—OSO₃H |
| 86 | HO₃SOC₂H₄O₂S—(o-tolyl) | 5-methyl-isoindolin-1-one-2-yl—C₃H₆SO₂C₂H₄OSO₃H |

EXAMPLE 87 a) 32 g of the compound of the formula

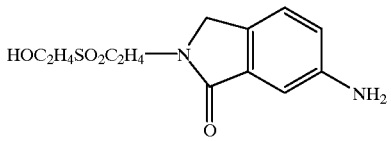

were stirred in 300 ml of water and 30 ml of 30% by weight hydrochloric acid and, after cooling with 100 g of ice, diazotized with 30 ml of 3.33 N aqueous sodium nitrite solution. After stirring at 0–5° C. for 30 minutes, the small excess of nitrous acid was destroyed with sulfamic acid, and the diazonium salt solution was mixed with a solution of 10.7 g of m-toluidine in 100 ml of water and 10 ml of 30% by weight hydrochloric acid. The pH was adjusted to 1.5 with saturated sodium acetate solution, and the mixture was kept at room temperature overnight. The hydrochloride of the dye of the formula

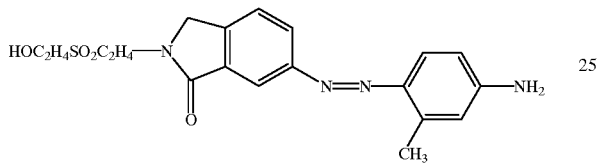

was filtered off with suction, washed with aqueous hydrochloric acid and dried at 60° C. under reduced pressure.

b) 30 g of the compound described in a) were stirred into 200 g of concentrated sulfuric acid and kept at 40° C. for 3 h until the sulfuric ester had substantially been produced.

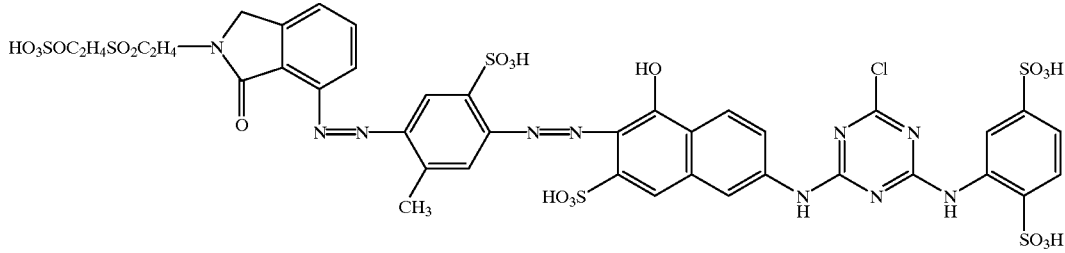

Sulfonation occurred by adding 90 g of 65% by weight oleum and stirring at 80° C. for two hours. The resulting dye of the formula

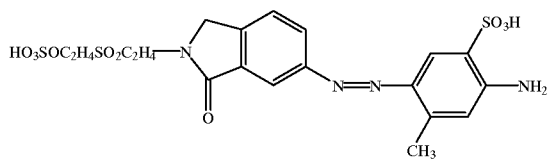

was stirred into 1000 g of ice and filtered off with suction.

c) The material on the filter from Example 87b, which was wet and contained sulfuric acid, was stirred in 150 ml of water and, at 10–15° C., 11 ml of 3.33 N aqueous sodium nitrite solution were added. After stirring at 10–15° C. for 30 minutes, the excess nitrous acid was destroyed, and a solution of 24 g of the compound of the formula

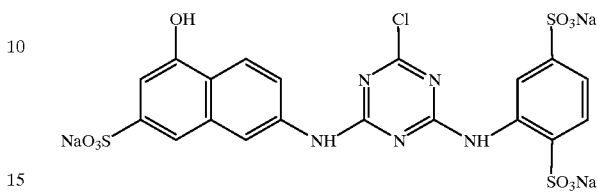

in 150 ml of water was added to the diazonium salt solution. Buffering with aqueous sodium acetate solution to pH 5 resulted in coupling to give the dye of the formula which was isolated as sodium salt. It dyes cotton in clear brick-red hues with a good fastness profile.

EXAMPLE 88

A solution of the product of the reaction of cyanuric chloride with H acid (as described in 52a)) was coupled to the anchor compound described in Example 1b) under the conditions given therein. Addition of 5.4 g of p-phenylenediamine was followed by stirring at room temperature and pH 6 for about 6 hours.

After heating to 40° C. and at pH 5, the condensation was complete, resulting in a dye of the formula

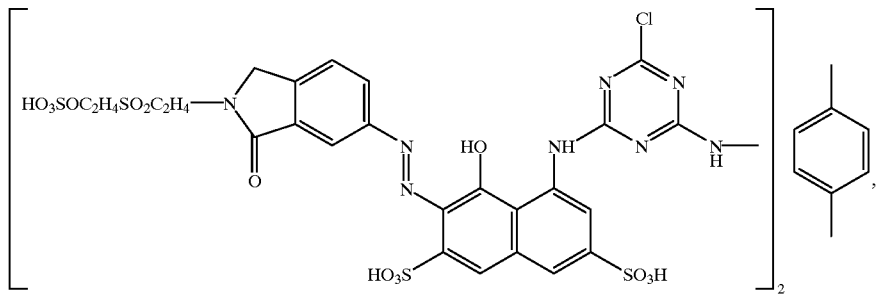

The dye was precipitated with sodium chloride, filtered off with suction, washed with 15% by weight brine and dried at 40° C. under reduced pressure. It dyes cotton in a bluish red hue with high brilliance and a very high color yield.

EXAMPLE 89

Initially the dye of the formula

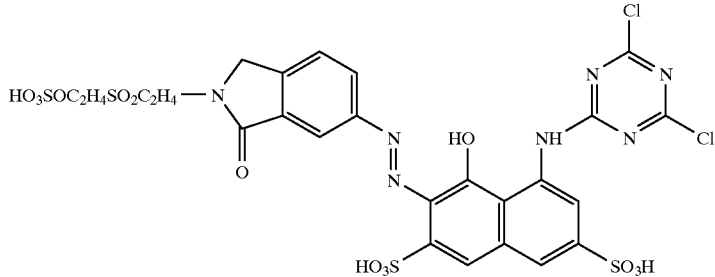

obtained in Example 88 by coupling was condensed with the equivalent amount of 2-methylamino-4-aminobenzenesulfonic acid at pH 5 and at 25° C. Then it was reacted with the dye of the formula

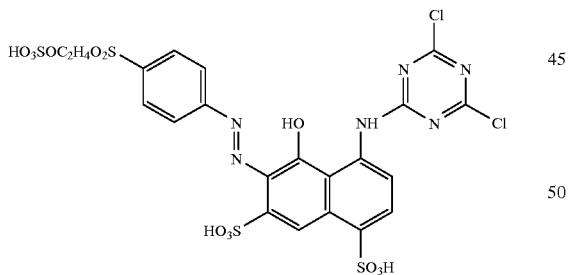

described in Example 72a) under identical reaction conditions. The dye of the formula

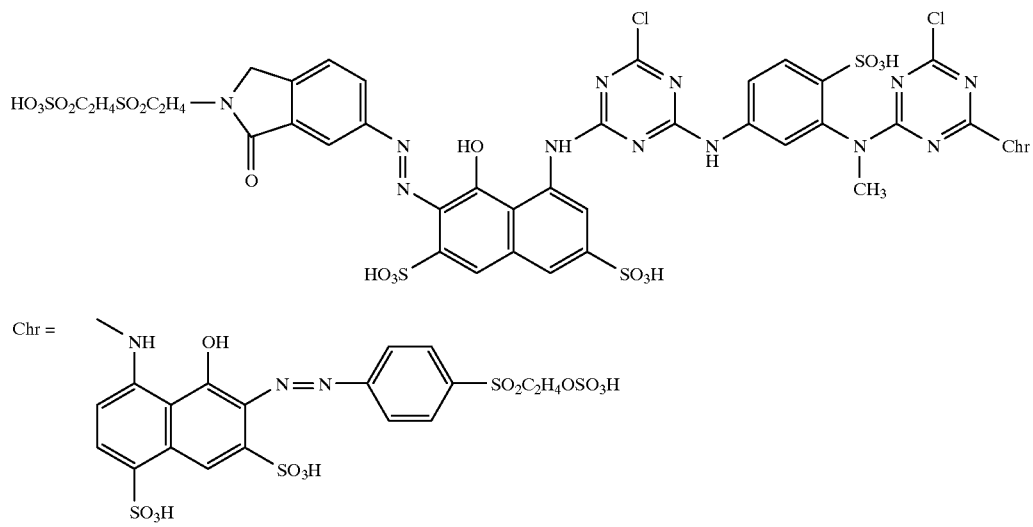
was obtained in high yield. It dyes cotton in a neutral red hue.
The dyes listed in the following Tables 5 and 6 are obtained in a similar way.

TABLE 5-continued

Structure:

D¹—N=N—K¹—(triazine with Cl)—T—(triazine with Cl)—K²—N=N—D²

T = 
$$\left( -N(CH_3)- \underset{SO_3H}{\underset{|}{C_6H_3}} -NH- \right)$$
(2-SO₃H, with N(CH₃) and NH substituents on benzene ring)

| Ex. No. | D¹ | K¹ | K² | D² | Hue |
|---|---|---|---|---|---|
| 92 | HO₃SOC₂H₄SO₂C₂H₄–(6-methyl-isoindolin-1-on-2-yl) | 1-hydroxy-2-methyl-6-amino-naphthalene-3-sulfonic acid (HO, CH₃, HO₃S, NH) | 8-amino-1-hydroxy-2-methyl-naphthalene-3,5-disulfonic acid (NH, OH, SO₃H, SO₃H) | SO₂C₂H₄OSO₃H (2-methylphenyl) | yellowish red |
| 93 | HO₃SOC₂H₄SO₂C₂H₄–(6-methyl-isoindolin-1-on-2-yl) | 8-amino-1-hydroxy-2-methyl-naphthalene-3,6-disulfonic acid | 8-amino-1-hydroxy-2-methyl-naphthalene-3,5-disulfonic acid | 2-methylnaphthalene-1,5-disulfonic acid (SO₃H, SO₃H) | bluish red |
| 94 | HO₃SOC₂H₄SO₂C₂H₄–(6-methyl-isoindolin-1-on-2-yl) | 8-amino-1-hydroxy-2-methyl-naphthalene-3,5-disulfonic acid | 8-amino-1-hydroxy-2-methyl-naphthalene-3,6-disulfonic acid | 2-methylphenyl-SO₃H | red |
| 95 | HO₃SOC₂H₄SO₂C₂H₄–(6-methyl-isoindolin-1-on-2-yl) | 8-amino-1-hydroxy-2-methyl-naphthalene-3,6-disulfonic acid | 8-amino-1-hydroxy-2-methyl-naphthalene-3,6-disulfonic acid | HO₃SOC₂H₄SO₂C₂H₄–(6-methyl-isoindolin-1-on-2-yl) | red |

TABLE 6
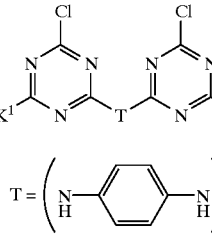
| Ex. No. | D¹ | K¹ | K² | D² | Hue |
|---|---|---|---|---|---|
| 96 | HO₃SOC₂H₄SO₂C₂H₄ 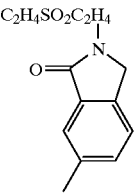 | 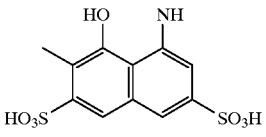 | 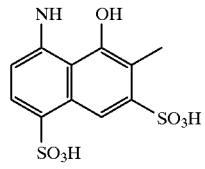 | 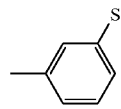 SO₂C₂H₄OSO₃H | red |
| 97 | HO₃SOC₂H₄SO₂C₂H₄ 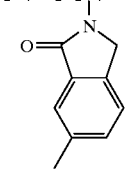 | 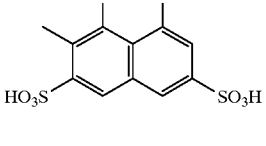 | 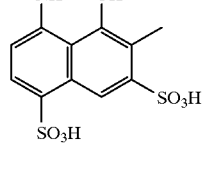 | 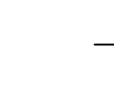 SO₂C₂H₄OSO₃H | red |
| 98 | HO₃SOC₂H₄SO₂C₂H₄ 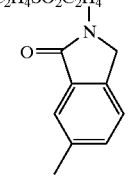 | 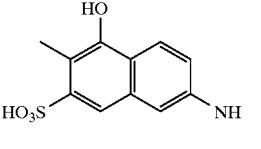 | 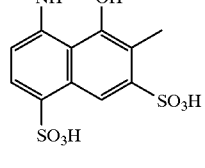 | 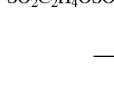 SO₂C₂H₄OSO₃H | yellowish red |
| 99 | HO₃SOC₂H₄SO₂C₂H₄ 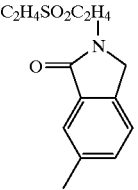 | 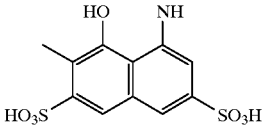 | 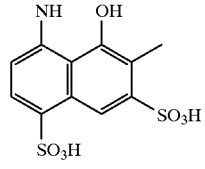 | 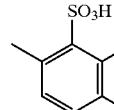 | bluish red |
| 100 | HO₃SOC₂H₄SO₂C₂H₄ 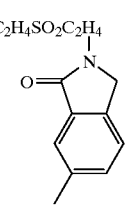 | 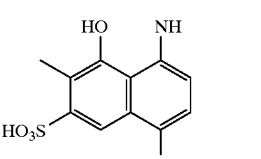 | 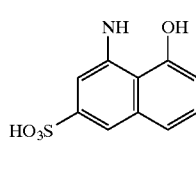 | 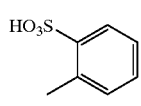 | red |
| 101 | HO₃SOC₂H₄SO₂C₂H₄ 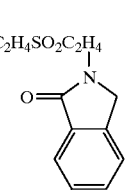 | 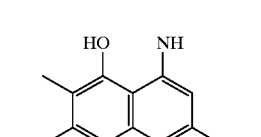 | 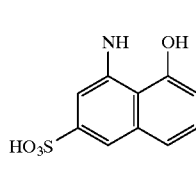 | HO₃SOC₂H₄O₂SC₂H₄ 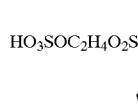 | red |

EXAMPLE 102

42 g of bromaminic acid, 56 g of the compound of the formula

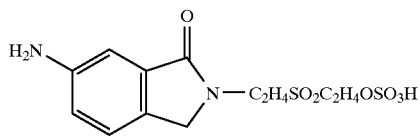

3 g of copper(I) chloride and 21 g of sodium bicarbonate in 400 ml of water were slowly heated to 50° and stirred at 50° C. for a further 5 h. Cooling to 5° C. and filtration with suction were followed by washing with 10% by weight aqueous sodium chloride solution. Drying under reduced pressure resulted in 57 g of the dye of the formula

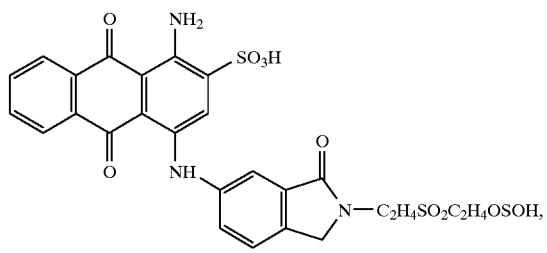

which dyes cotton in a brilliant blue hue.

EXAMPLE 103

25 g of copper phthalocyaninetetrasulfonyl chloride were suspended in 250 ml of ice-water. To this were added 38 g of the compound of the formula

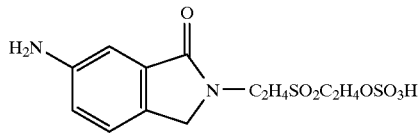

and 0.8 g of nicotinamide, and the pH was adjusted to 6.0–6.5 with 10% by weight aqueous sodium bicarbonate solution. The reaction mixture was stirred at room temperature for 8 h, during which the pH was kept at 6.0–6.5 by further addition of aqueous sodium bicarbonate solution. After filtration to clarify, the dye was precipitated by adding acetone, and was filtered off with suction and dried. 52 g of the dye of the formula

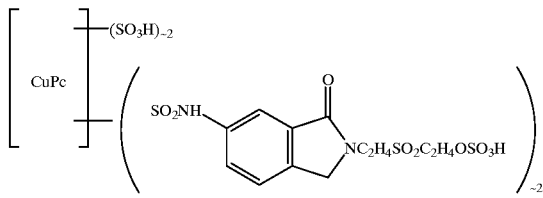

were isolated, and this dyes cotton in brilliant greenish blue hues.

EXAMPLE 104

40.0 g of the compound of the formula

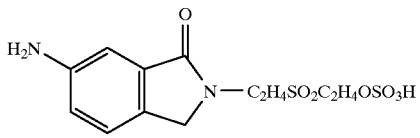

were suspended in 250 ml of water at 0–5° C. The pH was reduced to 1 with 18% by weight hydrochloric acid and then diazotization was carried out by dropwise addition of 30 ml of 3.33 N aqueous sodium nitrite solution.

After stirring at 0–5° C. for 30 minutes, the slight excess of nitrite was removed with sulfamic acid, and then 19.6 g of the pyridone of the formula

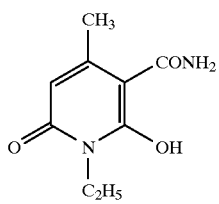

were added to the suspension of the diazonium salt.

The pH was raised to 4.5–5.5 by adding sodium carbonate, and the mixture was then stirred at 0–5° C. and the same pH for 4 h until coupling was complete.

Precipitation with 100 g of sodium chloride, filtration with suction and drying under reduced pressure resulted in 74 g of electrolyte-containing dye of the formula

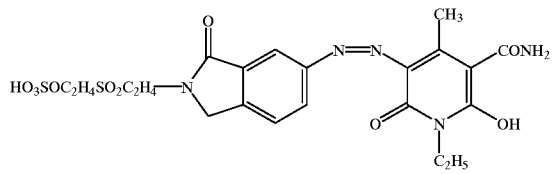

($\lambda_{max}$ (water): 418 nm).

The dyes listed in the following Table 7 are obtained as in Example 104.

TABLE 7

[Structure: Y¹—O₂S—X—N(isoindolinone)—N=N—(pyridone with CH₃, R¹, OH, =O, N-R²)]

| Ex. | R¹ | R² | X | Y¹ | Hue |
|---|---|---|---|---|---|
| 105 | H | C₂H₅ | CH₂CH₂ | CH₂CH₂OSO₃H | greenish yellow |
| 106 | CN | C₂H₅ | CH₂CH₂ | CH₂CH₂OSO₃H | greenish yellow |
| 107 | CH₂SO₃H | C₂H₅ | CH₂CH₂ | CH₂CH₂OSO₃H | greenish yellow |
| 108 | CONH₂ | C₂H₅ | CH₂CH₂CH₂ | CH₂CH₂Cl | greenish yellow |
| 109 | CONH₂ | —C₆H₄—SO₃H | CH₂CH₂ | CH₂CH₂OSO₃H | greenish yellow |
| 110 | CH₂SO₃H | —C₆H₄—SO₃H | CH₂CH₂ | CH₂CH₂OSO₃H | greenish yellow |
| 111 | CONH₂ | —C₆H₄—SO₂CH₂CH₂OSO₃H | CH₂CH₂ | CH₂CH₂OSO₃H | greenish yellow |
| 112 | SO₃H | C₂H₅ | CH₂CH₂ | CH₂CH₂OSO₃H | greenish yellow |
| 113 | CH₂SO₃H | CH₂CH₂NH—(triazine-Cl)—NH—C₆H₄(m-SO₃H) | CH₂CH₂ | CH₂CH₂OSO₃H | greenish yellow |
| 114 | CH₂SO₃H | CH₂CH₂NH—(triazine-Cl)—NH—C₆H₄(p-SO₂CH₂CH₂OSO₃H) | CH₂CH₂ | CH₂CH₂OSO₃H | greenish yellow |

EXAMPLE 115

The procedure was similar to Example 104 but the pyrazole compound of the formula

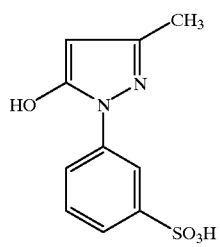

was used as coupling component and, after precipitation with sodium chloride, filtration with suction and drying under reduced pressure, the dye of the formula

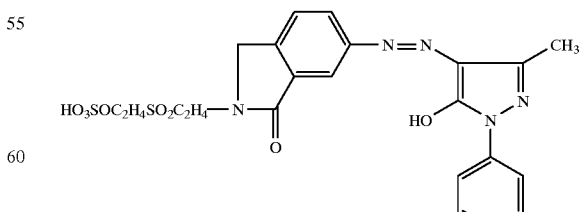

was obtained, and this dyes cotton by the processes customary for reactive dyes in clear greenish yellow hues.

The dyes listed in the following Table 8 can be obtained using comparable coupling components.

TABLE 8

Structure: HO₃SOC₂H₄SO₂C₂H₄—N(isoindolin-1-one)—N=N—K

| Ex. No. | K | Hue |
|---|---|---|
| 116 | 3-carboxy-4-methyl-5-hydroxy-1-(4-sulfophenyl)pyrazole | yellow |
| 117 | 4,6-dihydroxy-5-methyl-2-hydroxypyrimidine | greenish yellow |
| 118 | 4-amino-5-methyl-6-hydroxy-2-morpholinopyrimidine | yellow |
| 119 | 3-carboxy-4-methyl-5-hydroxy-1-[4-(2-sulfatoethylsulfonyl)phenyl]pyrazole | greenish yellow |
| 120 | CH₃CO—CH(CH₃)—CO—HN—(2-methoxy-4-methyl-5-sulfophenyl) | greenish yellow |
| 121 | CH₃CO—CH(CH₃)—CO—HN—(2-(2-sulfatoethylsulfonylethyl)-isoindolin-1-on-6-yl) | greenish yellow |

TABLE 8-continued

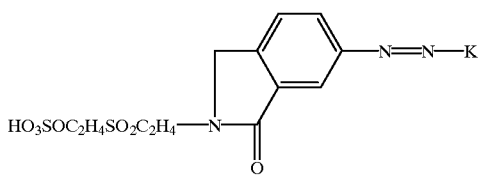

| Ex. No. | K | Hue |
|---|---|---|
| 122 | ![structure with SO3H, NH2, HNCOCH3] | golden yellow |
| 123 | ![structure with N(CH2CH2OSO3H)2, Cl] | orange |
| 124 | ![structure with N(CH2CH2SO2CH2OSO3H)2, Cl] | orange |

EXAMPLE 125

54.8 g of the dye of the formula

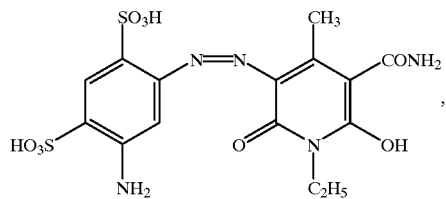

obtained by diazotization of 2,4-diaminobenzene-1,5-disulfonic acid and coupling at pH 5 with 1-ethyl-2-hydroxy-3-carbamoyl-4-methyl-6-pyridone, were dissolved in 350 ml of water at pH 5.5 and cooled to 0–5° C. Subsequently 18.4 g of cyanuric chloride dissolved in 100 ml of acetone were added dropwise and then the mixture was stirred at 0–5° C. for 3 h until reaction was complete. During the dropwise addition and subsequent stirring, the pH was kept at 5.0–5.5 by adding 5% by weight aqueous sodium bicarbonate solution.

After adding 48 g of the compound of the formula

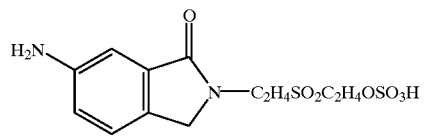

the mixture was heated to 40–45° C. and then stirred at this temperature for 5 h, keeping the pH at 5.5–6.0 with 5% by weight aqueous sodium bicarbonate solution.

Precipitation with 200 g of sodium chloride, filtration with suction and drying resulted in the dye of the formula

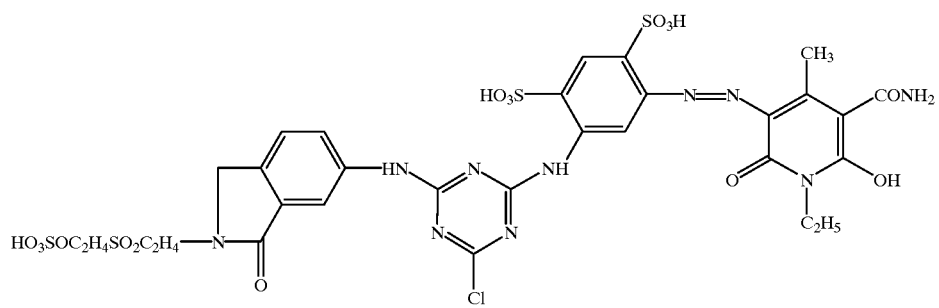

which dyes cotton either by the exhaust process at 40–50° C. or the cold pad-batch process in greenish yellow hues.

The dyes listed in the following Table 9 were obtained in a similar manner.

TABLE 9

General structure:

$Y^1-O_2S-X-N(\text{isoindolinone})-NH-[\text{triazine with Hal}]-D-N=N-K$

| Ex. No. | X | Hal | $Y^1$ | D | K | Hue |
|---------|---|-----|-------|---|---|-----|
| 126 | $CH_2CH_2$ | Cl | $CH_2CH_2OSO_3H$ | 4-amino-2-methyl-phenyl-1-sulfonic acid (NH-linked, $SO_3H$) | 1-ethyl-3-methyl-4-carbamoyl-6-hydroxy-pyridin-2-one | greenish yellow |
| 127 | $CH_2CH_2$ | Cl | $CH_2CH_2OSO_3H$ | 4-(N-methylamino)-2-methyl-phenyl-1-sulfonic acid | 1-ethyl-3-methyl-4-carbamoyl-6-hydroxy-pyridin-2-one | greenish yellow |
| 128 | $CH_2CH_2$ | Cl | $CH_2CH_2OSO_3H$ | 4-amino-2-methyl-5-sulfo-phenyl-1-sulfonic acid ($HO_3S$, $SO_3H$, $NH$) | 1-ethyl-3-methyl-4-(sulfomethyl)-6-hydroxy-pyridin-2-one ($CH_2SO_3H$) | greenish yellow |
| 129 | $CH_2CH_2$ | F | $CH_2CH_2OSO_3H$ | 4-amino-2-methyl-5-sulfo-phenyl-1-sulfonic acid | 1-ethyl-3-methyl-4-(sulfomethyl)-6-hydroxy-pyridin-2-one ($CH_2SO_3H$) | greenish yellow |
| 130 | $CH_2CH_2$ | F | $CH_2CH_2OSO_3H$ | 4-amino-2-methyl-5-sulfo-phenyl-1-sulfonic acid | 1-ethyl-3-methyl-4-carbamoyl-6-hydroxy-pyridin-2-one ($CONH_2$) | greenish yellow |

TABLE 9-continued

Structure:

Y¹—O₂S—X—N(ring)—...—NH—[triazine with Hal]—D—N=N—K where the isoindolinone bears a C=O and the triazine has Hal substituent.

| Ex. No. | X | Hal | Y¹ | D | K | Hue |
|---|---|---|---|---|---|---|
| 131 | CH₂CH₂CH₂ | Cl | CH₂CH₂OSO₃H | 2,5-disulfo-4-amino-methylphenyl (SO₃H, HO₃S, NH, CH₃) | 1-(C₂H₄OSO₃H)-2-OH-3,5-dimethyl-4-CONH₂-6-oxo-pyridine | greenish yellow |
| 132 | CH₂CH₂ | Cl | CH₂CH₂OSO₃H | 2,5-disulfo-4-amino-methylphenyl (SO₃H, HO₃S, NH, CH₃) | 1-[4-(SO₂C₃H₄OSO₃H)phenyl]-2-OH-3,5-dimethyl-4-CONH₂-6-oxo-pyridine | greenish yellow |
| 133 | CH₂CH₂ | Cl | CH₂CH₂OSO₃H | 4-amino-2-methyl-phenyl-SO₃H | 1-[4-(SO₂C₂H₄OSO₃H)phenyl]-3-methyl-4-methyl-5-hydroxy-pyrazole | reddish yellow |
| 134 | CH₂CH₂ | Cl | CH₂CH₂OSO₃H | 4-amino-2-methyl-phenyl-SO₃H | CH₃COCH(—)CONH—C₆H₄—SO₂C₂H₄OSO₃H (acetoacetanilide type) | greenish yellow |

EXAMPLE 135

85.1 g of the dye of the formula

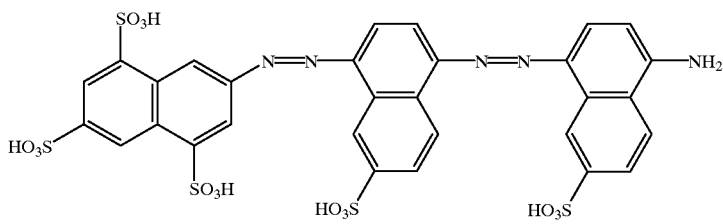

were introduced into 750 ml of water at 0–5° C. and pH 5.5. Then 18.4 g of cyanuric chloride dissolved in 150 ml of acetone were added dropwise, during which the pH was kept at 5.0–5.5 by adding 5% by weight aqueous sodium bicarbonate.

After reaction was complete, 50.5 g of the compound of the formula

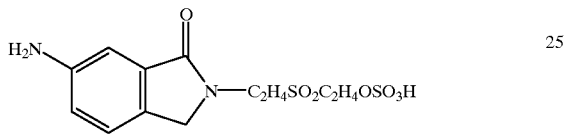

were added, and the temperature was raised to 35–40° C. The mixture was stirred at 35–40° C. for 5 h, during which the pH was kept at 5.5–6.0 with 5% by weight aqueous sodium bicarbonate solution.

Precipitation with 200 g of sodium chloride, filtration with suction and drying resulted in the dye of the formula

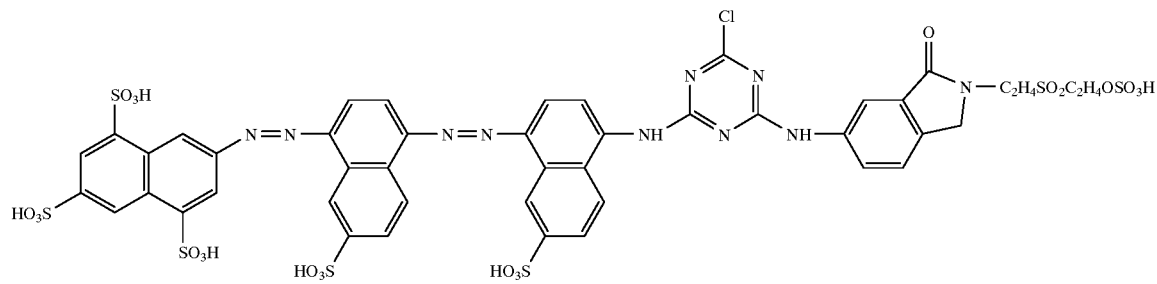

which dyes cotton by the processes customary for reactive dyes in reddish brown hues.

The dyes listed in the following Table 10 are obtained in a similar manner.

TABLE 10

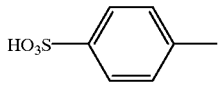

| Ex. No. | D | K¹ | K² | Hal | Hue |
|---|---|---|---|---|---|
| 136 | 4-HO₃S-C₆H₄- (p-sulfophenyl) | 2,5-dimethyl-phenyl-4-SO₃H | 4,8-dimethyl-naphthyl-1-SO₃H | Cl | yellowish brown |
| 137 | 2,4-disulfo-5-methyl-phenyl | 4,8-dimethyl-6-sulfo-naphthyl | 4,8-dimethyl-6,7-sulfo-naphthyl | Cl | reddish brown |
| 138 | 3-methyl-1,5-disulfo-naphthyl | 4,8-dimethyl-6,7-sulfo-naphthyl | 4,8-dimethyl-naphthyl-1-SO₃H | F | reddish brown |
| 139 | 3-methyl-1,5-disulfo-naphthyl | 4,8-dimethyl-6-sulfo-naphthyl | 2,5-dimethyl-phenyl-HNCONH₂ | Cl | reddish brown |
| 140 | 4-(HO₃SOC₂H₄SO₂)-phenyl | 4,8-dimethyl-6-sulfo-naphthyl | 4,8-dimethyl-6-sulfo-naphthyl | Cl | reddish brown |
| 141 | 3-methyl-1,5-disulfo-naphthyl | 2,4,5-trimethyl-phenyl | 4,8-dimethyl-naphthyl-1-SO₃H | Cl | yellowish brown |

EXAMPLE 142 a) 50.6 g of the compound of the formula

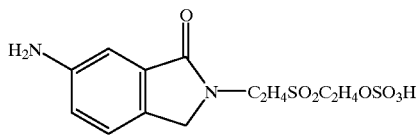

were diazotized as in Example 104, and 17.9 g of Cleve's beta acid in neutral solution in 100 ml of water were added. The pH was then adjusted to 4.5–5.0 with saturated aqueous sodium acetate solution, and the mixture was stirred at room temperature for 24 h until coupling was complete.

The pH was reduced with 18% by weight of hydrochloric acid. After cooling to 0–5° C., diazotization was carried out by adding 30 ml of 3.33 N aqueous sodium nitrite solution as described in Example 104.

After diazotization was complete, a further 17.9 g of Cleve's beta acid in neutral solution in 100 ml of water were added. The pH was then raised to 4.0, and the mixture was stirred at room temperature for 25 h until coupling was complete.

Precipitation with ethanol, filtration with suction and drying under reduced pressure resulted in 80 g of electrolyte-containing dye of the formula

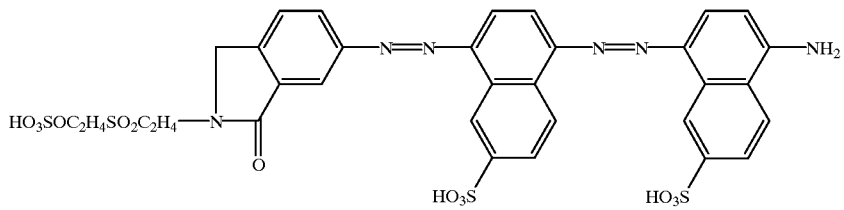

b) 80 g of the dye described in a) were reacted as in Example 125 with cyanuric chloride and the compound of the formula

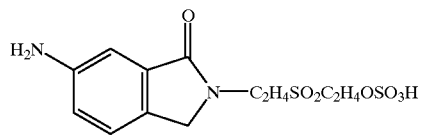

to give the dye of the formula

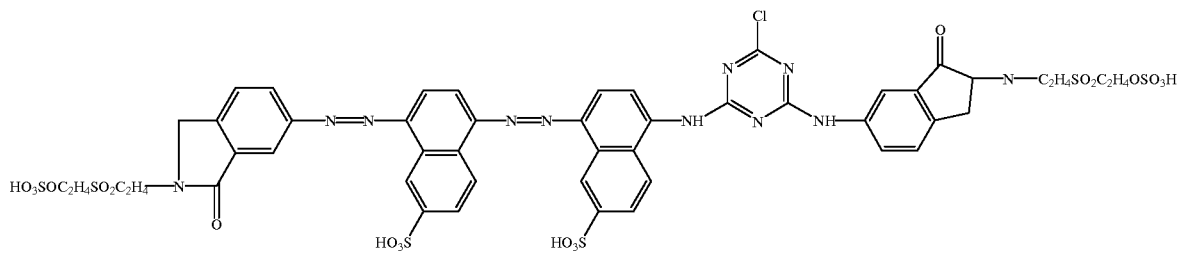

The dyes listed in the following Table 11 are obtained in a similar manner to Example 142.

TABLE 11
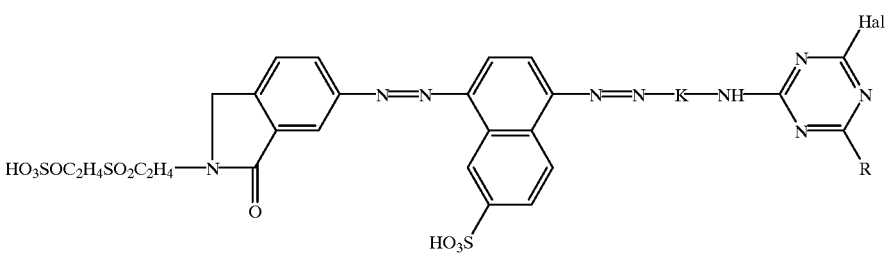
| Ex. No. | K | Hal | R | Hue |
|---|---|---|---|---|
| 143 | 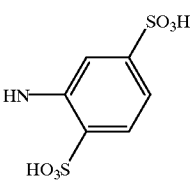 | Cl | 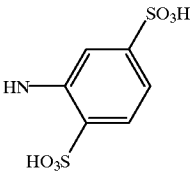 | brown |
| 144 | 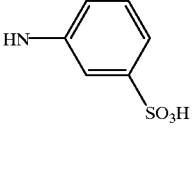 | Cl | 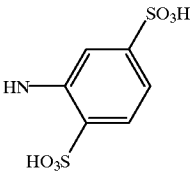 | brown |
| 145 | 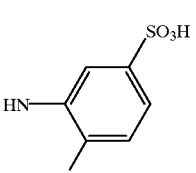 | F | 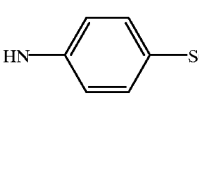 | brown |
| 146 | 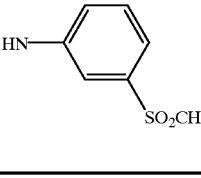 | Cl | 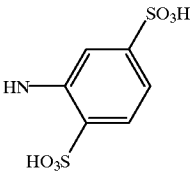 | brown |
| 147 | 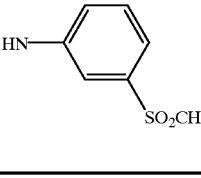 | Cl | 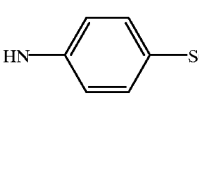 | brown |
| 148 | 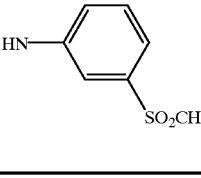 | Cl | 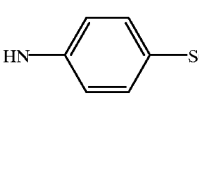 | brown |
EXAMPLE 149
To a suspension of 75 g of the dichlorotriazine dye of the formula

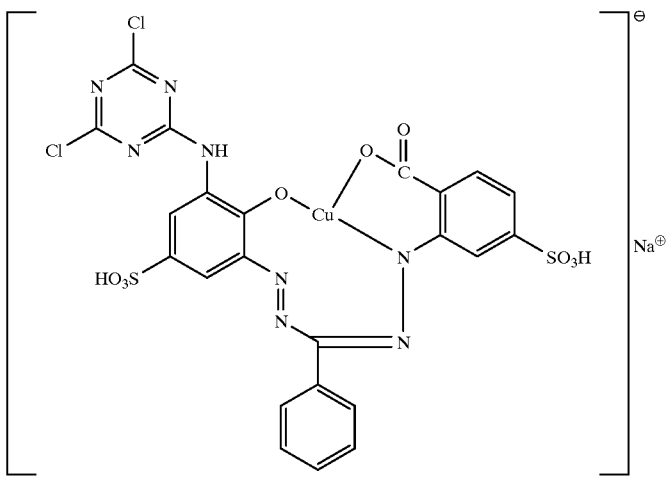

in 600 ml of water was added, at pH 7, a solution of 40 g of the compound of the formula

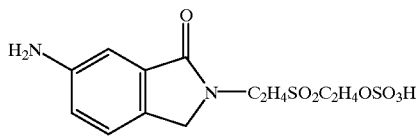

in 600 ml of water. The suspension was heated to 40–45° C. and the pH was kept neutral by adding sodium bicarbonate. After 2.5 h, the dye of the formula which had formed was salted out with 250 g of sodium chloride, filtered off and dried. The resulting dark blue dye powder dyes cotton in a clear blue hue. The dyeings are fast to light and wet and display remarkable stability to oxidative effects.

The dyes listed in the following Table 12 can be obtained as in Example 149.

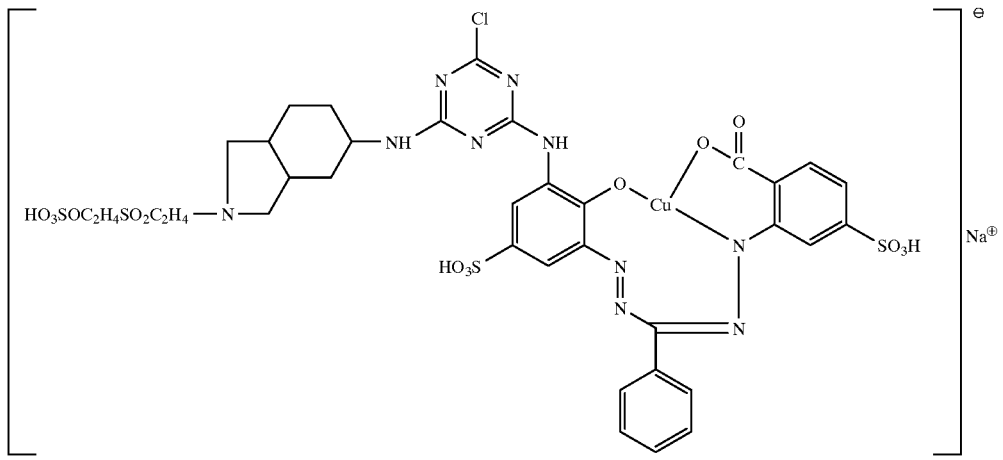

λmax (water): 618 nm

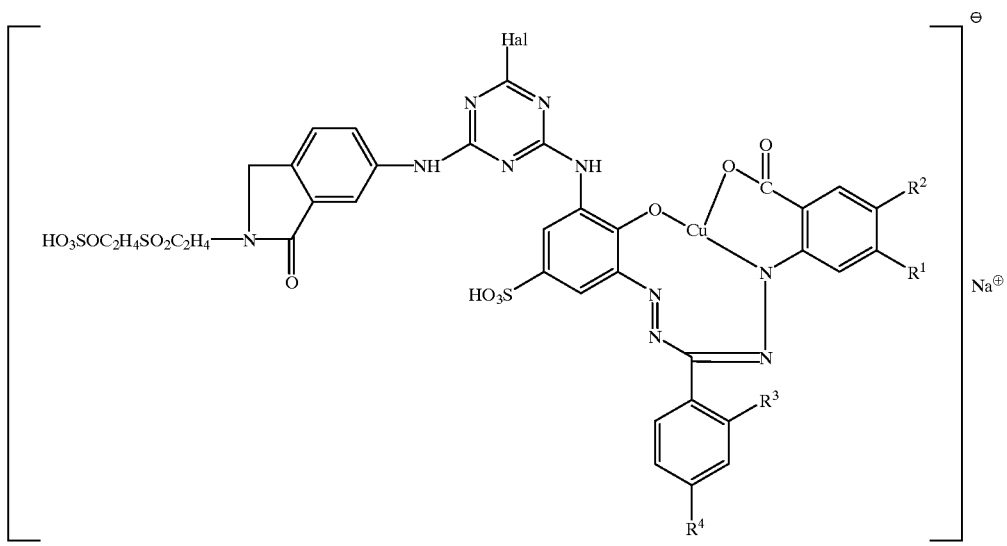

| Ex. No. | R¹ | R² | R³ | R⁴ | Hal |
|---|---|---|---|---|---|
| 150 | H | SO₃H | H | H | F |
| 151 | SO₃H | H | H | H | Cl |
| 152 | H | SO₃H | SO₃H | H | Cl |
| 153 | H | SO₃H | H | SO₂CH₂CH₂Cl | Cl |
| 154 | H | NHCOCBr=CH₂ | SO₃H | H | Cl |
| 155 | H | SO₂CH₂CH₂OSO₃H | SO₃H | H | Cl | until the reaction was complete, which took about 1 h. After cooling to room temperature and salting out with 500 g of sodium chloride the precipitated dye was filtered off with suction and dried. It dyes cotton in a brilliant blue hue with good fastness properties and corresponds to the formula

EXAMPLE 156

19.1 g of the compound of the formula

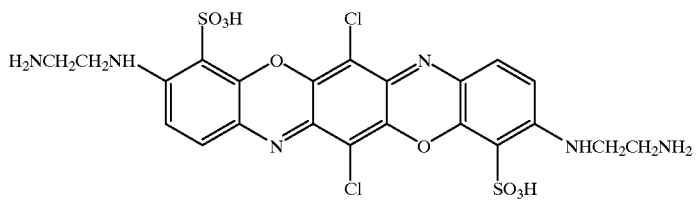

were stirred into 1000 ml of water, adjusting the pH to 10 with sodium hydroxide solution. This solution was added dropwise to a solution of the condensate of 11.1 g of cyanuric chloride with 24 g of the compound of the formula

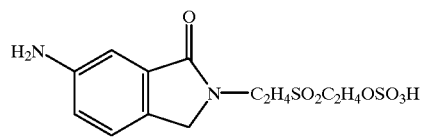

which was adjusted to pH 6–8 and was at 40–50° C. The mixture was stirred at 60° C. while maintaining pH 6.5–7

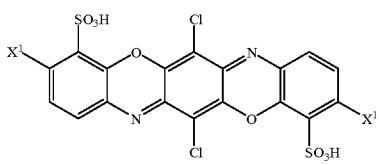

$X^1$ = HO₃SOC₂H₄SO₂H₄—

λmax (water): 615 nm

Further dyes obtained in a similar way are listed in Table 13.

TABLE 13

[Structural formula shown at top of table]

| Ex. No. | Y¹ | Y² | R | Hal | n | X | Hue |
|---|---|---|---|---|---|---|---|
| 157 | HNCH$_2$CH$_2$NH | Y¹ | SO$_3$H | F | 1 | CH$_2$CH$_2$CH$_2$ | blue |
| 158 | HNCH$_2$CH$_2$NH | Y¹ | SO$_2$CH$_2$CH$_2$OSO$_3$H | Cl | 1 | CH$_2$CH$_2$ | blue |
| 159 | HNCH$_2$CH$_2$N(CH$_2$CH$_2$OSO$_3$H) | Y¹ | SO$_2$CH$_2$CH$_2$OSO$_3$H | Cl | 1 | CH$_2$CH$_2$ | blue |
| 160 | HN-C$_6$H$_4$-NH | Y¹ | SO$_3$H | Cl | 1 | CH$_2$CH$_2$ | blue |
| 161 | HNCH$_2$CH$_2$CH$_2$NH | Y¹ | SO$_3$H | Cl | 1 | CH$_2$CH$_2$ | blue |
| 162 | HNCH$_2$CH$_2$CH$_2$NH | Y¹ | SO$_3$H | F | 1 | CH$_2$CH$_2$ | blue |
| 163 | OCH$_2$CH$_2$NH | Y¹ | SO$_3$H | Cl | 1 | CH$_2$CH$_2$ | red |
| 164 | O-C$_6$H$_4$-NH | Y¹ | SO$_3$H | Cl | 1 | CH$_2$CH$_2$ | red |
| 165 | HNCH$_2$CH$_2$CH$_2$NH | Y¹ | SO$_3$H | F | 1 | CH$_2$CH$_2$ | blue |
| 166 | HNCH$_2$CH$_2$CH$_2$NH | NH$_2$ | SO$_3$H | Cl | 0 | CH$_2$CH$_2$ | blue |
| 167 | HNCH$_2$CH$_2$CH$_2$NH | NH$_2$ | SO$_2$CH$_2$CH$_2$OSO$_3$H | Cl | 0 | CH$_2$CH$_2$ | blue |
| 168 | HNCH$_2$CH$_2$CH$_2$NH | NHCH$_2$CH$_2$OSO$_3$H | SO$_2$CH$_2$CH$_2$OSO$_3$H | Cl | 0 | CH$_2$CH$_2$ | blue |

EXAMPLE 169

394 g of hydroxyethoxyethylamine and 402 g of phthalide were heated over the course of 2 h to 200–210° C. and the resulting water distilled out. The reaction was complete after 3 h. The excess amine was removed by distillation under 20 bar, and 605 g of the compound

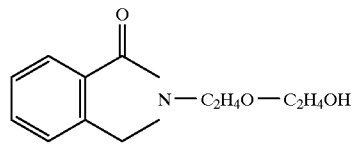

were isolated.

M.p.: 72–75°

EXAMPLE 170

605 g of the compound from Example 169 were heated with 333 g of thionyl chloride in 1000 g of toluene to 60–65° C. After cooling, the mixture was poured into 3000 g of water, and the organic phase was separated off. After removal of the toluene by distillation, 600 g of an oil remained. (Cl content: 14.5%; calculated for Cl: 14.8%)

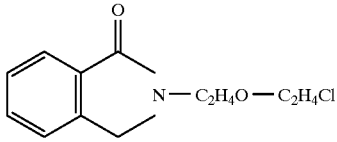

EXAMPLE 171

1000 g of bromobenzene, 292.5 g of 2-mercaptoethanol and 300 g of 50% sodium hydroxide solution were heated at 60–70° C. for 1 h. Then 718.5 g of the compound from Example 170 were added, during which the temperature rose to 90° C. After 3 h at 95–100° C., 1000 g of water were added, and the bromobenzene phase was separated off and concentrated. 738 g of the compound

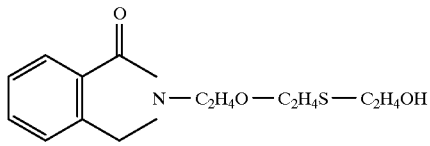

were isolated.

EXAMPLE 172

2 g of tungstic acid were added to a suspension of 703 g of the compound from Example 171 in 500 g of water and, at 65 to 85° C., 567 g of a 30% strength solution of $H_2O_2$ were added dropwise. After the reaction was complete, 2000 g of ethanol were added, and the residue was filtered off. Concentration resulted in 820 g of the compound

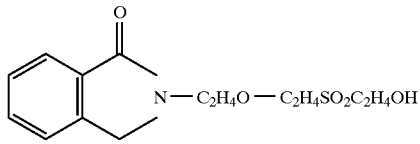

being isolated.

NMR ($d_6$-DMSO): 3.20 ppm (t, 2); 3.40 (m, 2); 3.75 (m, 8); 4.58 (s, 2); 5.07 (t, 1); 7.60 (m, 4).

EXAMPLE 173

485 g of Example 172 were dissolved at 20 to 40° C. in 1519 g of 100% strength sulfuric acid. After 3 h at 35 to 40° C., the mixture was cooled to 0 to 5° C., and a solution of 107.5 g of 100% strength nitric acid in 300 g of 96% strength sulfuric acid was added dropwise over the course of 2 h. After a further 5 h, the reaction mixture was poured into 6420 g of ice-water. The pH was adjusted to 4.0 by adding solid calcium carbonate. The precipitate was filtered off with suction and discarded. The mother liquor was concentrated to about 4000 g at <35° C. and under 14 mbar. 400 g of isopropanol, 100 parts of glacial acetic acid and 5 g of a Pd catalyst were added, and hydrogen was passed in at 50–55° C. After hydrogen uptake was complete and removal of the catalyst by filtration, the volume was reduced under 14 mbar and at 35° C. to about 1500 ml. The solution contains the compound

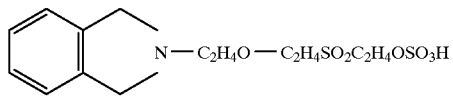

and is used in this form for the dye synthesis.

We claim:

1. A reactive dye of the formula I

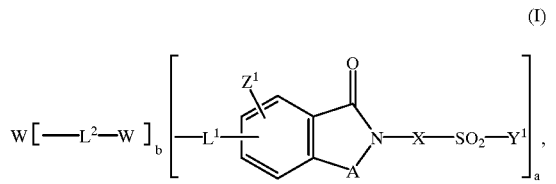

where a is 1 or 2;

b is 0 or 1;

$Z^1$ is hydrogen, $C_1$–$C_6$-alkyl, $C_1$–$C_6$-alkoxy, halogen, nitro, amino, hydroxysulfonyl, $C_1$–$C_6$-alkoxycarbonyl; carbamoyl or $C_1$–$C_6$-mono- or dialkylcarbamoyl, A is methylene, sulfonyl or a radical of the formula $CH_2$—CO or $CH_2$—$SO_2$, with the methylene group being linked in each case to the benzene ring;

X is a direct linkage, $C_1$–$C_8$-alkylene which is or is not interrupted via 1 to 3 oxygen atoms in ether functionality, 1 to 3 imino groups or 1 to 3 $C_1$–$C_4$-alkylimino groups, or a radical of the formula $L^3$—CO—$NZ^2$—$L^4$, where $L^3$ and $L^4$ are each, independently of one another, $C_1$–$C_4$-alkylene and $Z^2$ is hydrogen, $C_1$–$C_6$-alkyl or phenyl; and $Y^1$ is vinyl or a radical of the formula $C_2H_4Q$ where Q is a group which is eliminatable under alkaline conditions;

W is in case 1) the radical of a chromophore which has no or further reactive groups and which is derived from a metallized or nonmetallized mono- or disazo dye, a triphendioxazine, an anthraquinone, a metallized formazan or a metallized phthalocyanine, or in case 2) the radical of a coupling component to which additionally the radical of a diazo component is or is not linked via an azo bridge and which may or may not have additional reactive groups, $L^1$ is in case 1) a linker of the formula $O_2S$—$NZ^3$, OC—$NZ^3$, $Z^3N$—$O_2S$, $Z^3N$—OC, $Z^3N$—OC—$NZ^4$, $NZ^3$ or 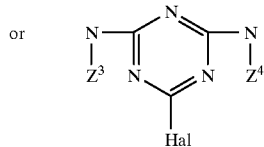

where $Z^3$ and $Z^4$ are each, independently of one another, hydrogen, $C_1$–$C_6$-alkyl or phenyl and Hal is fluorine, chlorine or bromine or $NZ^3$ or $NZ^4$ is also piperazine-1,4-diyl, or in case 2) an azo bridge and $L^2$ is a radical of the formula

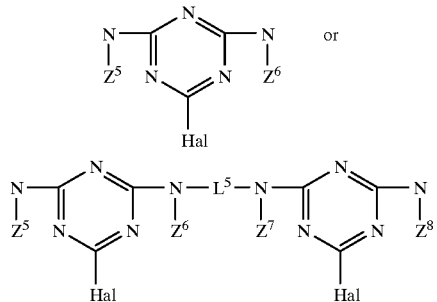

where $Z^5$, $Z^6$, $Z^7$ and $Z^8$ are each, independently of one another, hydrogen, $C_1$–$C_6$-alkyl or phenyl and $L^5$ is $C_2$–$C_8$-alkylene or phenylene which is unsubstituted or substituted by $C_1$–$C_4$-alkyl, $C_1$–$C_4$-alkoxy or hydroxysulfonyl, and Hal has in each case the above-mentioned meaning.

2. A reactive dye as claimed in claim 1, wherein A is methylene, or the radical of the formula $CH_2$—CO.

3. A reactive dye as claimed in claim 1, wherein X is $C_1$–$C_8$-alkylene which is uninterrupted or is interrupted by 1 to 3 oxygen atoms in ether functionality.

4. A reactive dye as claimed in claim 1, wherein $Z^1$ is hydrogen.

5. The reactive dye according to claim 1, wherein said group A of formula (I) is selected from the group consisting of methylene and a radical of the formula $CH_2$—CO.

6. A method comprising dyeing or printing substrates having hydroxyl groups or nitrogen atoms with a reactive dye as claimed in claim 1.

* * * * *